United States Patent
Bernstein et al.

(10) Patent No.: US 10,631,979 B2
(45) Date of Patent: Apr. 28, 2020

(54) TRANSCATHETER STENT AND VALVE ASSEMBLY

(71) Applicant: PECA Labs, Inc., Etna, PA (US)

(72) Inventors: C. Douglas Bernstein, Pittsburgh, PA (US); Arush Kalra, Pittsburgh, PA (US); Denver Faulk, North Huntingdon, PA (US)

(73) Assignee: PECA Labs, Inc., Pittsburgh, PA (US)

( * ) Notice: Subject to any disclaimer, the term of this patent is extended or adjusted under 35 U.S.C. 154(b) by 0 days.

(21) Appl. No.: 15/729,545

(22) Filed: Oct. 10, 2017

(65) Prior Publication Data

US 2018/0098844 A1    Apr. 12, 2018

Related U.S. Application Data

(60) Provisional application No. 62/406,175, filed on Oct. 10, 2016, provisional application No. 62/532,736, filed on Jul. 14, 2017.

(51) Int. Cl.
*A61F 2/24* (2006.01)
*A61F 2/30* (2006.01)

(52) U.S. Cl.
CPC .......... *A61F 2/2418* (2013.01); *A61F 2/2415* (2013.01); *A61F 2/2463* (2013.01); *A61F 2/2409* (2013.01); *A61F 2/2427* (2013.01); *A61F 2002/30011* (2013.01); *A61F 2210/0014* (2013.01); *A61F 2220/0008* (2013.01); *A61F 2230/0054* (2013.01)

(58) Field of Classification Search
CPC ...................................................... A61F 2/24
See application file for complete search history.

(56) References Cited

U.S. PATENT DOCUMENTS

| | | | |
|---|---|---|---|
| 4,160,688 A | 7/1979 | Brooks et al. | |
| 4,187,390 A | 2/1980 | Gore | |
| 4,475,972 A | 10/1984 | Wong | |
| 4,816,339 A * | 3/1989 | Tu | A61F 2/06 428/421 |
| 4,955,899 A | 9/1990 | Della Corna et al. | |
| 5,443,499 A | 8/1995 | Schmitt | |
| 5,466,261 A | 11/1995 | Richelsoph | |

(Continued)

FOREIGN PATENT DOCUMENTS

| | | |
|---|---|---|
| CN | 1304298 A | 7/2001 |
| CN | 101896139 A | 11/2010 |

(Continued)

OTHER PUBLICATIONS

Famaey, In Situ Evolution of the Mechanical Properties of Stretchable and Non-Stretchable Eptfe Vascular Grafts and Adjacent Native Vessels, Int J Artif Organs 2014; 37 (12): 900-910.

(Continued)

*Primary Examiner* — Jacqueline Woznicki
(74) *Attorney, Agent, or Firm* — Pepper Hamilton LLP

(57) ABSTRACT

Valves constructed from low porosity leaflets are disclosed. The valves disclosed herein may be integrated into a variety of structures, such as valved conduits and transcatheter stents, and may be constructed of one or more layers. Embodiments herein are also directed to methods of using the same and methods of making the same.

22 Claims, 22 Drawing Sheets

Surface Porosity

(56) References Cited

U.S. PATENT DOCUMENTS

| | | | |
|---|---|---|---|
| 5,469,868 A | 11/1995 | Reger | |
| 5,800,512 A | 9/1998 | Lentz et al. | |
| 5,804,011 A | 9/1998 | Dutta et al. | |
| 5,824,050 A * | 10/1998 | Karwoski | C08L 27/18 623/1.4 |
| 5,843,161 A | 12/1998 | Solovay | |
| 6,016,848 A | 1/2000 | Egres, Jr. | |
| 6,436,135 B1 | 8/2002 | Goldfarb | |
| 6,517,571 B1 | 2/2003 | Brauker et al. | |
| 6,716,239 B2 | 4/2004 | Sowinski et al. | |
| 6,863,686 B2 | 3/2005 | Shannon et al. | |
| 6,939,372 B2 | 9/2005 | Dong | |
| 7,153,324 B2 | 12/2006 | Case et al. | |
| 7,153,325 B2 | 12/2006 | Kim et al. | |
| 7,306,729 B2 | 12/2007 | Bacino et al. | |
| 7,789,908 B2 | 9/2010 | Sowinski et al. | |
| 8,672,997 B2 | 3/2014 | Drasler et al. | |
| 8,900,652 B1 | 12/2014 | Caballero et al. | |
| 9,585,746 B2 | 3/2017 | Yoshida et al. | |
| 10,182,907 B2 | 1/2019 | Lapeyre | |
| 2001/0039450 A1 | 11/2001 | Pavcnik et al. | |
| 2002/0022879 A1 | 2/2002 | Samkov et al. | |
| 2002/0052651 A1 | 5/2002 | Myers et al. | |
| 2002/0055775 A1 | 5/2002 | Carpentier et al. | |
| 2002/0072794 A1 | 6/2002 | Gabbay | |
| 2002/0133226 A1 | 9/2002 | Marquez et al. | |
| 2002/0138135 A1 | 9/2002 | Duerig et al. | |
| 2002/0173842 A1 | 11/2002 | Buchanan | |
| 2003/0027332 A1 | 2/2003 | Lafrance et al. | |
| 2003/0114924 A1 | 6/2003 | Moe | |
| 2003/0139805 A1 | 7/2003 | Holmberg et al. | |
| 2003/0191525 A1 | 10/2003 | Thornton | |
| 2004/0249451 A1 | 12/2004 | Lu et al. | |
| 2005/0049697 A1 | 3/2005 | Sievers | |
| 2005/0075727 A1 | 4/2005 | Wheatley | |
| 2005/0096734 A1 | 5/2005 | Majercak et al. | |
| 2005/0137682 A1 * | 6/2005 | Justino | A61F 2/2412 623/1.24 |
| 2005/0228495 A1 | 10/2005 | Macoviak | |
| 2005/0240262 A1 | 10/2005 | White | |
| 2005/0283224 A1 | 12/2005 | King | |
| 2006/0122693 A1 | 6/2006 | Biadillah et al. | |
| 2006/0149366 A1 | 7/2006 | Henderson | |
| 2006/0161248 A1 | 7/2006 | Case et al. | |
| 2006/0229716 A1 | 10/2006 | Mitrev | |
| 2006/0259136 A1 | 11/2006 | Nguyen et al. | |
| 2006/0265053 A1 | 11/2006 | Hunt | |
| 2006/0287717 A1 | 12/2006 | Rowe et al. | |
| 2007/0027528 A1 | 2/2007 | Agnew | |
| 2007/0043431 A1 | 2/2007 | Melsheimer | |
| 2007/0067021 A1 | 3/2007 | Haverkost et al. | |
| 2008/0206442 A1 | 8/2008 | Shekalim et al. | |
| 2009/0118826 A1 | 5/2009 | Khaghani | |
| 2010/0023114 A1 | 1/2010 | Chambers et al. | |
| 2010/0023120 A1 | 1/2010 | Holecek et al. | |
| 2010/0204775 A1 | 8/2010 | Edwin | |
| 2010/0312333 A1 | 12/2010 | Navia et al. | |
| 2011/0060401 A1 | 3/2011 | Hoerstrup et al. | |
| 2011/0071625 A1 | 3/2011 | Hill et al. | |
| 2011/0094592 A1 | 4/2011 | Cheng et al. | |
| 2011/0098800 A1 | 4/2011 | Braido et al. | |
| 2011/0125163 A1 | 5/2011 | Rutten et al. | |
| 2011/0166637 A1 | 7/2011 | Irwin et al. | |
| 2012/0158125 A1 | 6/2012 | Obradovic | |
| 2012/0271396 A1 | 10/2012 | Zheng et al. | |
| 2012/0290082 A1 | 11/2012 | Quint et al. | |
| 2013/0013058 A1 | 1/2013 | Umezu et al. | |
| 2013/0019756 A1 | 2/2013 | Yoshida et al. | |
| 2013/0166016 A1 | 6/2013 | Cully et al. | |
| 2013/0184807 A1 | 7/2013 | Kovach et al. | |
| 2013/0261739 A1 * | 10/2013 | Kuehn | A61F 2/2412 623/2.11 |
| 2013/0304196 A1 | 11/2013 | Kelly | |
| 2013/0319603 A1 | 12/2013 | Wu | |
| 2014/0005772 A1 * | 1/2014 | Edelman | A61F 2/2412 623/2.17 |
| 2014/0031924 A1 | 1/2014 | Bruchman et al. | |
| 2014/0031927 A1 | 1/2014 | Bruchman et al. | |
| 2014/0131268 A1 | 5/2014 | Abusleme et al. | |
| 2014/0155995 A1 | 6/2014 | Sun et al. | |
| 2014/0288642 A1 * | 9/2014 | Yoshida | A61L 27/16 623/2.17 |
| 2014/0330372 A1 | 11/2014 | Weston et al. | |
| 2015/0366664 A1 | 12/2015 | Guttenberg et al. | |
| 2016/0015516 A1 | 1/2016 | Bernstein et al. | |
| 2016/0067038 A1 | 3/2016 | Park et al. | |
| 2016/0100939 A1 * | 4/2016 | Armstrong | A61F 2/2412 623/2.12 |
| 2017/0252156 A1 | 3/2017 | Bernstein et al. | |
| 2017/0196685 A1 | 7/2017 | Yoshida et al. | |
| 2018/0098845 A1 | 4/2018 | Bernstein et al. | |
| 2018/0168795 A1 | 6/2018 | Bernstein et al. | |

FOREIGN PATENT DOCUMENTS

| | | |
|---|---|---|
| CN | 102497836 A | 6/2012 |
| JP | S6446468 A | 2/1989 |
| JP | 2007-536951 A | 12/2007 |
| JP | 2008526366 A | 7/2008 |
| WO | 1994015548 A1 | 7/1994 |
| WO | 2005011535 A2 | 2/2005 |
| WO | 2009061419 A1 | 5/2009 |
| WO | 2009134701 A2 | 11/2009 |
| WO | 2012018779 A2 | 2/2012 |
| WO | 2013/019756 A2 | 2/2013 |
| WO | 2014/138599 A1 | 9/2014 |
| WO | 2014145811 A1 | 9/2014 |
| WO | 2016205773 A1 | 12/2016 |
| WO | 2017151900 A1 | 9/2017 |
| WO | 2018071417 A1 | 4/2018 |

OTHER PUBLICATIONS

Pashneh-Tala, The Tissue-Engineered Vascular Graft—Past, Present, and Future; International Standard 2016, Tissue Engineering: Part B, vol. 22, No. 1, 2016: 68-100.

Back et al. Biomaterials in Vascular Surgery; Human Biomaterials Applications. Humana Press, Inc., 1996: 257-299.

International Standard for Cardiovascular implants and extracorporeal systems—Vascular prostheses—Tubular vascular grafts and vascular patches (ISO 7198:1-54 (2016)).

International Search Report and Written Opinion for International application No. PCT/US2017/055939, dated Feb. 5, 2018.

Cantanese et al. "Mechanical Properties of Medical Grade Expanded Polytetrafluorothylene: The Effect of Internodal Distance, Density, and Displacement Rate". Apr. 24, 1998. Journal of Biomedial Materials Research, 48: 187-192.

Yuan et al., Right ventricular outflow tract reconstruction: valve conduit of choice and clinical outcomes, J Cardiovasc Med, (2008), 9(4):327-337.

Ando et al., Ten-year experience with handmade trileaflet polytetrafluoroethylene valved conduit used for pulmonary reconstruction, J Thorac Cadiovasc Surg, (2009), 137:124-131.

Batlivala et al., Pulmonary Valve Replacement Function in Adolescents: A Comparison of Bioprosthetic Valves and Homograft Conduits, Ann Thorac Surg, (2012), 93:2007-2016.

Bernstein et al., Bicuspid-Valved PTFE Conduit Optimization for Pediatric RVOT Reconstruction, Bioengineering Conference (NEBEC), (2011).

Bianca et al., Sex ratio imbalance in transposition of the great arteries and possible agricultural environmental risk factors, Images Paediatr Cardiol, (2001), 8:10-14.

Bielefeld et al., Reoperative Homograft Right Ventricular Outflow Tract Reconstruction, Ann Thorac Surg, (2001), 71(2):482-488.

Boethig et al., Mid term course after pediatric right ventricular outflow tract reconstruction: a comparison of homografts, porcine xenografts and Contegras, European Journal of Cardio-thoracic Surgery, (2005), 27:58-66.

(56) References Cited

OTHER PUBLICATIONS

Boudjemline et al., Use of bovine jugular vein to reconstruct the right ventricular outflow tract: Early results, J Thorac Cardiovasc Surg, (2003), 126:490-497.
Brown et al., Right ventricular outflow tract reconstruction with polytetrafluoroethylene monocusp valve: A twelve-year experience, J Thorac Cardiovasc Surg, (2007), 133(5):1336-1343.
Caldarone et al., Independent Factors Associated with Longevity of Prosthetic Pulmonary Valves and Valved Conduits, J Thorac Cardiovasc Surg, (2000), 120:1022-1031.
Canfield et al., National Estimates and Race/Ethnic-Specific Variation of Selected Birth Defects in the United States, Birth Defects Research (Part A): Clinical and Molecular Teratology, (2006), 76:747-756.
Chrysosotomou et al., Chapter 21: Tetralogy of Fallot with Pulmonary Atresia, Critical Care of Children with Heart Disease: Basic Medical and Surgical Concepts, (2010), 213-219.
Chrysosotomou et al., Chapter 22: Pulmonary Atresia with Intact Interventricular Septum, Critical Care of Children with Heart Disease: Basic Medical and Surgical Concepts, (2010), 221-229.
Cruz et al., Truncus Arteriosus, Chapter 35, Critical Care of Children with Heart Disease, Springer, (2009).
DeFrances et al., National Hospital Discharge Survey: 2005 annual summary with detailed diagnosis and procedure data, National Center for Health Statistics, Vital Health Stat (2007), 13(165):1-218.
Dur et al., In Vitro Evaluation of Right Ventricular Outflow Tract Reconstruction With Bicuspid Valved Polytetrafluoroethylene Conduit, Artificial Organs, (2010), 34: 1010-1016.
Erek et al., Durability of Stentless Bioprostheses for Right Ventricular Outflow Tract Reconstruction, Ann Thorac Surg, (2005), 79(6): 2202-2203.
Forbess et al., Conduit selection for right ventricular outflow tract reconstruction: contemporary options and outcomes, Semin Thorac Cardiovasc Surg Pediatr Card Surg Annu, (2004), 7:115-124.
Forbess et al., Cryopreserved Homografts in the Pulmonary Position: Determinants of Durability, Ann Thorac Surg, (2001), 71(1):54-59.
Fung, Biodynamics-circulation, Springer-verlag, New York-Berlin-Heidelberg-Tokyo 1984, 404 p. 189.
Gober et al., Adverse Mid-Term Outcome Following RVOT Reconstruction Using the Contegra Valved Bovine Jugular Vein, Ann Thorac Surg, (2005), 79:625-631.
Graham et al, Comparison of Norwood Shunt Types: Do the Outcomes Differ 6 Years Later?, Ann Thorac Surg, (2010), 90:31-35.
Hamilton et al., Births: Preliminary Data for 2009, National Vital Statistics Reports, (Dec. 21, 2010), 59(3):1-19.
Heron et al., Deaths: Final Data for 2006, National Vital Statistics Reports, (Apr. 17, 2009), 57(14):1-135.
Hoffman, Chapter 21: Congenital Heart Disease, Essential Cardiology: Principles and Practice, 2nd Ed., 393-406.
Hoffman, The Incidence of Congenital Heart Disease, J. Am. Coll. Cardiol., (2002), 39(12):1890-1900.
Hoyert et al., Annual Summary of Vital Statistics: 2004, Pediatrics, (2006):168-183.
International Search Report and Written Opinion for PCT/US2014/021814 dated Jun. 25, 2014.
International Search Report and Written Opinion for PCT/US2012/048902 dated Oct. 5, 2012.
International Search Report and Written Opinion for PCT/US2017/020421 dated May 18, 2017.
Kaza et al., Long-term results of right ventricular outflow tract reconstruction in neonatal cardiac surgery: Options and outcomes, J Thorac Cardiovasc Surg, (2009), 138:911-916.
Menon et al., Regional Myocardial Dysfunction following Norwood with Right Ventricle to Pulmonary Artery Conduit in Patients with Hypoplastic Left Heart Syndrome, Journal of the American Society of Echocardiography, (2011), 24 (8):827-833.

Meyns et al., The Contegra conduit in the right ventricular outflow tract induces supravalvular stenosis, J Thorac Cardiovasc Surg, (2004), 128:834-840.
Miyazaki et al., Expanded polytetrafluoroethylene conduits and patches with bulging sinuses and fan-shaped valves in right ventricular outflow tract reconstruction: Multicenter study in Japan, J Thorac Cardiovasc Surg, (2011), 142:1122-1129.
Naheed et al., Chapter 16 Pulmonary Atresia with Intact Ventricular Septum, Heart Diseases in Children: A Pediatrician's Guide, (2011), 195-202.
Niwa et al., Progressive Aortic Root Dilation in Adults and Late After Repair of Tetralogy of Fallot, Circulation, (2002), 106:1374-1378.
Ohye, Comparison of Right Ventricle to Pulmonary Artery Conduit and Modified Blalock-Taussig Shunt Hemodynamics After the Norwood Operation, Ann Thorac Surg, (2004), 78:1090-1093.
Oury, The Ross Procedure: Currently Registry Results, Ann Thorac Surg, (1998), 66:S162-S165.
Parker et al., Updated National Birth Prevalence Estimates for Selected Birth Defects in the United States, 2004-2006, Birth Defects Research (Part A): Clinical and Molecular Tetratology, (2010), 88:1008-1016.
Proptopapas et al., Contegra conduit for reconstruction of the right ventricular outflow tract: a review of published early and mid-time results, Journal of Cardiothoracic Surgery, (2008), 3:62 (7 pages).
Rosti et al., Mechanical valves in the pulmonary position: a reappraisal, J Thorac Cardiovasc Surg, (1998), 115 (5):1074-1079.
Sano et al., Right ventricle-pulmonary artery shunt in first-stage palliation of hypoplastic left heart syndrome, J Thorac Cardiovasc Surg, (2003), 126:504-510.
Schreiber et al., Early Graft Failure of Small-Sized Porcine-Valved Conduits in Reconstruction of Right Ventricular Outflow Tract, Ann Thorac Surg, (2006), 82:179-186.
Shebani et al., Right ventricular outflow tract reconstruction using Contegra valved conduit: natural history and conduit performance under pressure, European Journal of Cardio-thoracic Surgery, (2006), 29:397-405.
Shiose et al., Recent Advances and Patents on Circulatory Support Devices for Pediatric Patients, Recent Patents on Biomedical Engineering, (2009), 2:161-164.
Stefano et al., Right ventricle outflow tract reconstruction in the pediatric population: A comparative analysis between different grafts, The 15th Congress on Cardio-Thoracic Surgery, (Nov. 2010).
Wald et al., Refining the assessment of pulmonary regurgitation in adults after tetralogy of Fallot repair: should we be measuring regurgitant fraction or regurgitant volume?, European Heart Journal, (2009), 30:356-361.
Wang et al., In vivo degradation characteristics of poly(glycerol sebacate), J Biomed Mater Res A, (2003), 66A:192-197.
Yoganathan et al., Fluid mechanics of heart valves, Annu Rev Biomed Eng, (2004), 6:331-362.
Yoshida et al., Midterm results of bicuspid valved PTFE conduit for right ventricular outflow tract reconstruction, The 48th Annual Meeting of STS (2012).
Yoshida et al., Right Ventricular Outflow Tract Reconstruction with Bicuspid Valved Polytetrafluoroethylene Conduit, Annals of Thoracic Surgery, (2011), 91:1235-1239.
Cantanese et al. "Mechanical Properties of Medical Grade Expanded Polytetrafluorothylene: The Effect of Internodal Distance, Density, and Displacement Rate". Apr. 24, 1998. Journal of Biomedical Materials Research, 48: 187-192.
Canadian Office Action for CA 2,855,943 dated Jul. 19, 2018.
Supplementary European Search Report and Written Opinion for EP 16812600 dated Jan. 15, 2019.
International Search Report and Written Opinion for PCT/US2016/038302 dated Sep. 7, 2016.
Canadian Office Action dated Jul. 19, 2018 for Canadian Patent Application No. 2,855,943.
Angiopiasty Balloons from Advanced Polymers by MedDevice Online, accessed Oct. 3, 2019 (published 2019).
BD Bard Conquest PTA Dilation Catheters, accessed Oct. 3, 2019 (published 2018).

(56) References Cited

OTHER PUBLICATIONS

Nordson Medical, Medical Balloon Types and Specifications, accessed Oct. 3, 2019 (published 2018).
Teleflex Medical OEM Balloons and Balloon Catheters, accessed Oct. 3, 2019 (published 2015).

* cited by examiner

FIG. 14A — Gore Preclude Membrane
FIG. 14B — PECA Leaflet Material
Side A
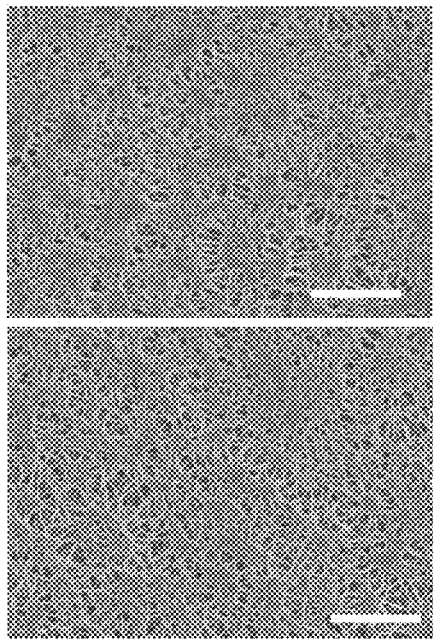
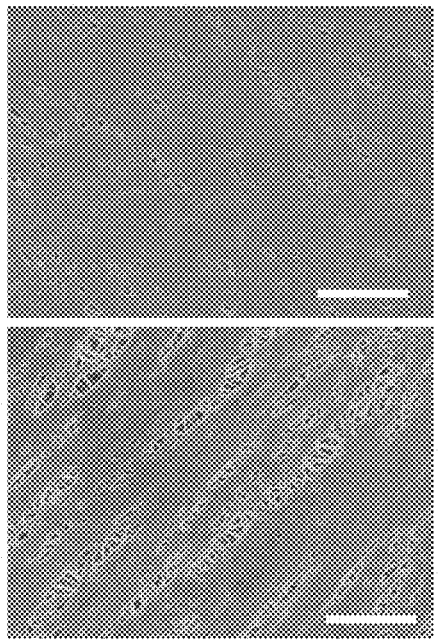
Side B
* Scale bar represents 5 μm
FIG. 14C
FIG. 14D FIG. 18A PECA Leaflet Material FIG. 18B
Side A            Side B
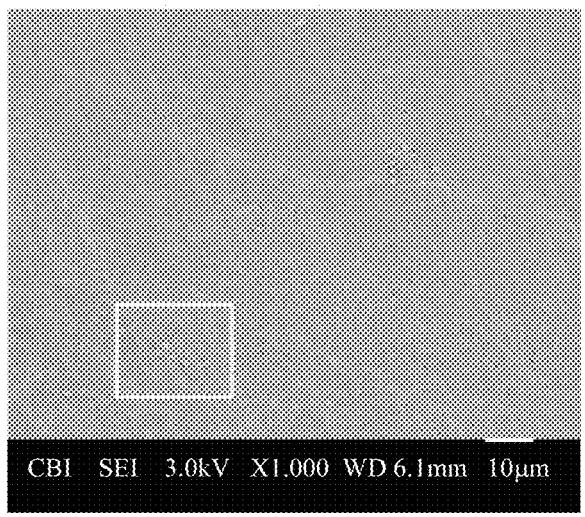
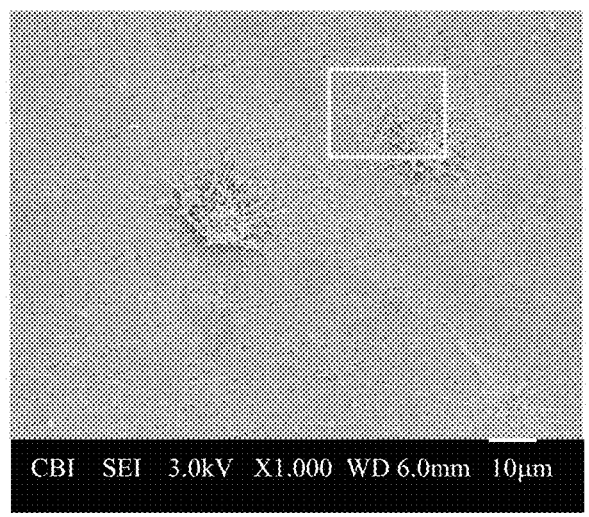
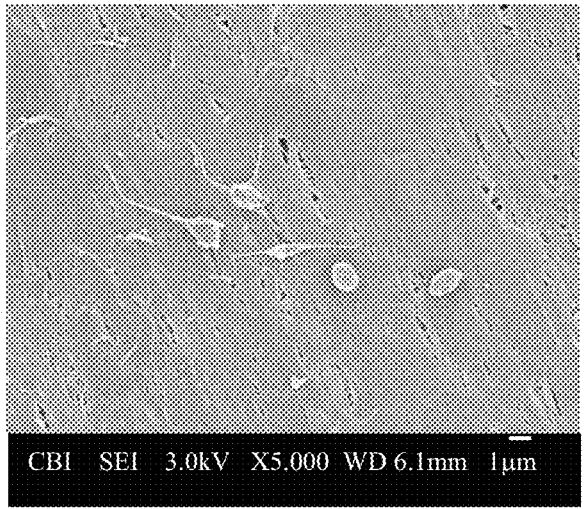
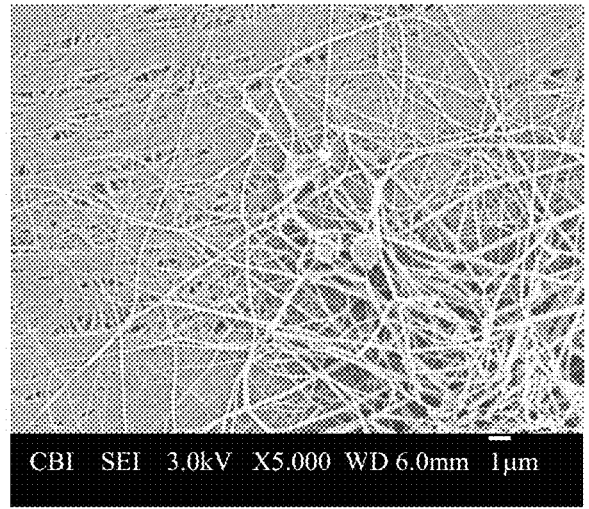
FIG. 18C                                      FIG. 18D FIG. 18E   Gore Preclude Membrane   FIG. 18F
Side A   Side B
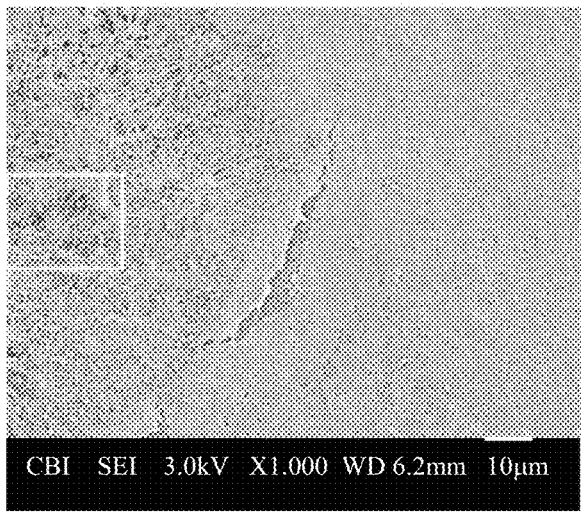
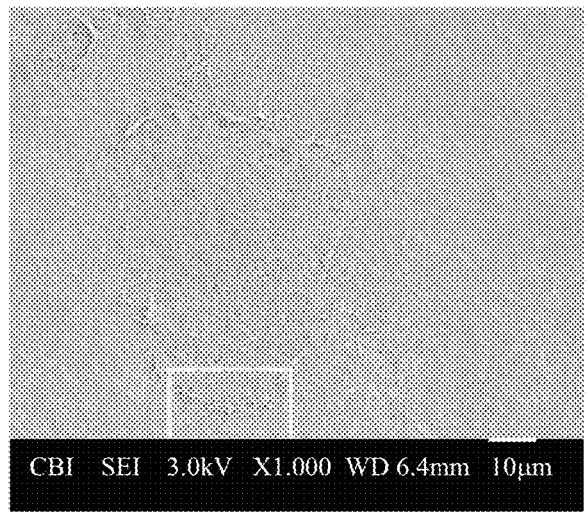
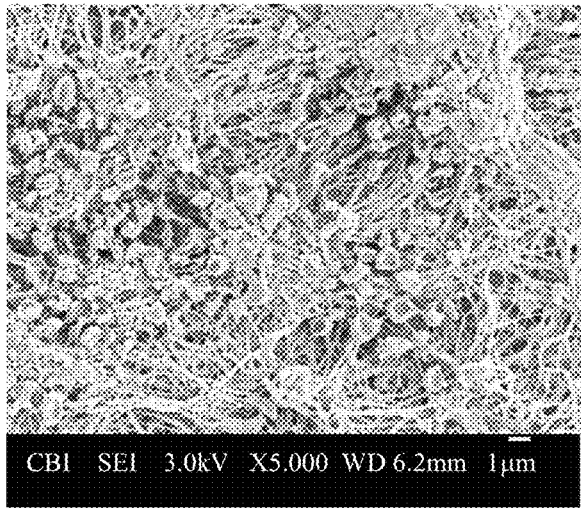
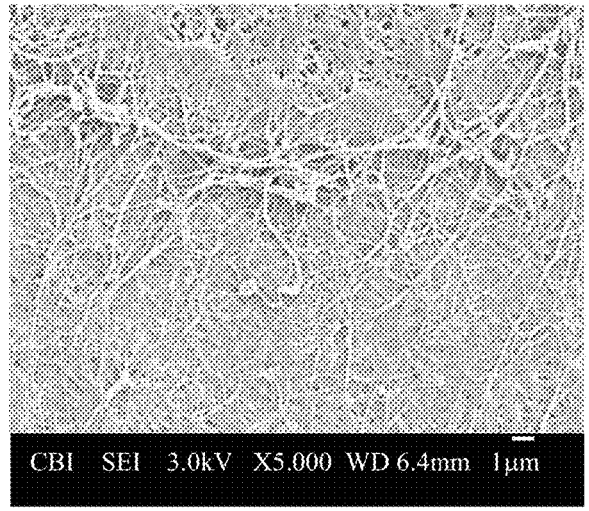
FIG. 18G   FIG. 18H

TRANSCATHETER STENT AND VALVE ASSEMBLY

CLAIM OF PRIORITY

This application claims priority from U.S. Provisional Application No. 62/406,175 entitled "Transcatheter Stent and Valve Assembly" filed on Oct. 10, 2016 and U.S. Provisional Application No. 62/532,736 entitled "Transcatheter Stent and Valve Assembly" filed on Jul. 14, 2017, the contents of each of which are incorporated by reference herein in its entirety.

SUMMARY

Various embodiments are directed to a valve including one or more leaflets, wherein each leaflet is constructed from a material which has a surface porosity of about 1% to less than 15%.

In some embodiments, a valve may include one or more leaflets, wherein each leaflet is constructed from more than one layer of a material. In some embodiments, at least two layers of the material can be anisotropic with orientations that are offset by an angle of at least 10 degrees.

In some embodiments, a valved conduit may include a conduit that has an inner surface and an outer surface, a valve that can be attached to the inner surface of the conduit at a plurality of attachment points, wherein the valve includes one or more leaflets, and wherein the one or more leaflets are constructed from a material which has a surface porosity of about 1% to less than 15%.

In some embodiments, a valved conduit may include a conduit having an inner surface and an outer surface, a valve attached to the inner surface of the conduit at a plurality of attachment points, the valve may further include one or more leaflets, wherein the one or more leaflets are constructed from more than one layer of a material, where at least two layers are anisotropic with orientations that are offset by an angle of at least 10 degrees.

In some embodiments, a valved conduit may include a fluoropolymer conduit having an inner surface and an outer surface, a valve attached to the inner surface of the fluoropolymer conduit at a plurality of attachment points. In some embodiments, the valve may further comprise one or more leaflets, wherein the one or more leaflets are constructed from at least two layers of a fluoropolymer which has a surface porosity of about 1% to about 7% and a total thickness of about 0.045 mm. In some embodiments, the at least two layers are anisotropic with orientations that offset by an angle of at least 10 degrees.

In some embodiments, a transcatheter stent may include a stent having chevron shaped structures disposed in two annular rows opposing each other, the stent may further include an inner surface and an outer surface and a collapsed configuration and an expanded configuration. In some embodiments, a valve can be attached to the inner surface of the stent at a plurality of attachment points, each attachment point being at a median vertex of the chevron shaped structure.

In some embodiments, a transcatheter stent may include a stent having a proximal portion and a distal portion, each portion may include a plurality of spindle-shaped structures, and an intermediate portion having chevron shaped structures disposed in annular rows opposing each other.

In some embodiments, a transcatheter stent may include a stent having chevron shaped structures disposed in two annular rows opposing each other, the stent may further include an inner surface and an outer surface and a collapsed configuration and an expanded configuration. In some embodiments, a valve can be attached to the inner surface of the stent at a plurality of attachment points, each attachment point being at a median vertex of the chevron shaped structure, or along a member which rotates during the transition between collapsed configuration and expanded configuration.

In some embodiments, a transcatheter stent may include a stent having chevron shaped structures disposed in two annular rows opposing each other, the stent may further include an inner surface and an outer surface and a collapsed configuration and an expanded configuration. In some embodiments, a valve can be attached to the inner surface of the stent at a plurality of attachment points, each attachment point being at a median vertex of the chevron shaped structure. In some embodiments, the valve may further include one or more leaflets constructed from at least two layers of a fluoropolymer, wherein the at least two layers are anisotropic with orientations that offset by an angle of at least 10 degrees.

BRIEF DESCRIPTION OF THE DRAWINGS

FIG. 14A is a SEM image of a Gore Preclude Membrane illustrating Side A of a material having a surface porosity.

FIG. 14B is a SEM image of a leaflet illustrating Side A of a material having a surface porosity.

FIG. 14C is a SEM image of a Gore Preclude Membrane illustrating Side B of a material having a surface porosity.

FIG. 14D is a SEM image of a leaflet illustrating Side B of a material having a surface porosity.

FIG. 18A depicts Side A of a leaflet having reduced thrombogenicity according to an embodiment.

FIG. 18B depicts Side B of a leaflet having reduced thrombogenicity according to an embodiment.

FIG. 18C depicts a magnified view of FIG. 18A.

FIG. 18D depicts a magnified view of FIG. 18B.

FIG. 18E depicts Side A of a Gore Preclude Membrane having thrombogenicity.

FIG. 18F depicts Side B of a Gore Preclude Membrane having thrombogenicity.

FIG. 18G depicts a magnified view of FIG. 18E.

FIG. 18H depicts a magnified view of FIG. 18F.

DETAILED DESCRIPTION

Figure 1A:
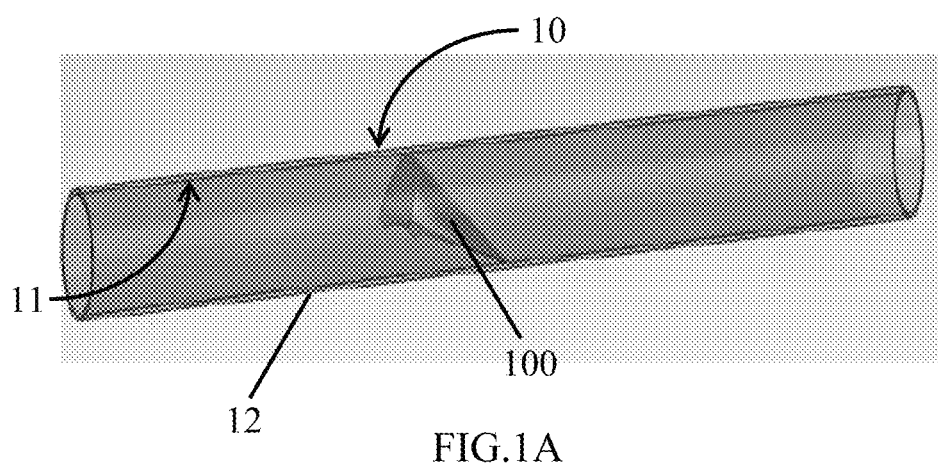
FIG. 1A shows a valved conduit in closed position.

Before the invention is described, it is to be understood that this invention is not limited to the particular systems, methodologies or protocols described, as these may vary. It is also to be understood that the terminology used herein is for the purpose of describing particular embodiments only, and is not intended to limit the scope of the present disclosure.

For the purpose of this disclosure, the term "plastically deformable material" means a material that may change its shape, size, or both shape and size in response to a deforming force placed thereon, and which does not fully recover its original shape, size, or both shape and size once the deforming force has been removed.

For the purpose of this disclosure, the term "elastic material" means a material that may change its shape, size, or both shape and size in response to a deforming force placed thereon, and which recovers its original shape, size, or both shape and size once the deforming force has been removed.

For the purpose of this disclosure, the term "yield strength" means the smallest deforming force that, when applied to a material, will result in a non-recoverable change in the shape, size, or both shape and size of the material.

For the purpose of this disclosure, the term "ultimate tensile strength" means the smallest deforming force that, when applied to a material, will result in a break or failure of the material.

As used herein, the term "about" means plus or minus 10% of the numerical value of the number with which it is being used. Therefore, about 50% means in the range of 45% to 55%.

As used herein, the term "surface porosity" means the total two-dimensional area of empty space in a given surface of a layer of material. Surface porosity is also referred to as surface percent porosity or pore area percent. Surface porosity is calculated by dividing the amount of empty space in a given two-dimensional area of a layer of material by the total two-dimensional area of that layer of material.

As used herein, the term "average pore area" means the average area of the pores in a layer of material having a plurality of pores. The average pore area is calculated by adding the pore area of the plurality of pores of a layer of material and dividing by the total number of pores in that layer of material.

As used herein, the term "pore diameter" means the longest diameter of a pore (major axis).

As used herein, the term "average pore diameter" means the average diameter of the pores in a one-layered or multi-layered material having a plurality of pores. The average pore diameter is calculated by adding the pore diameter of the plurality of pores of the one-layered or multi-layered material and dividing by the total number of pores therein.

As used herein, the term "total thickness" means the sum thickness of a conduit, a valve, or a leaflet having more than one layer of material.

As used herein, the term "rotate" means a movement which keeps a fixed point. This definition of rotation can apply within both two and three dimensions (in a plane and in space, respectively).

As used herein, the term "translation" means a movement which moves every point of a figure of a space by the same amount in a given direction.

As used herein, the term "non-stretching" means a material which has a strain less than 5%.

A valved conduit is a conduit having a valve disposed within it. A valved conduit is typically mounted on a stent before deployment. There are two types of stents on which the valved conduits are ordinarily mounted: a self-expanding stent and a balloon-expandable stent. To place such valved conduits and stents into a delivery apparatus and ultimately into a patient, the valved conduit and the stent must first be collapsed or crimped to reduce its circumferential size.

To date, the design and construction of these valved conduits have necessitated the use of a stretchable material in order to accommodate the change in shape that a conduit goes through between a collapsed state (for introduction through a small vessel) and an expanded state (for function in the final deployed position). Disclosed herein are transcatheter stents that substantially has same length between the collapsed state and the expanded state and aid in use of non-stretchable conduits and valve structures.

Figure 1B:
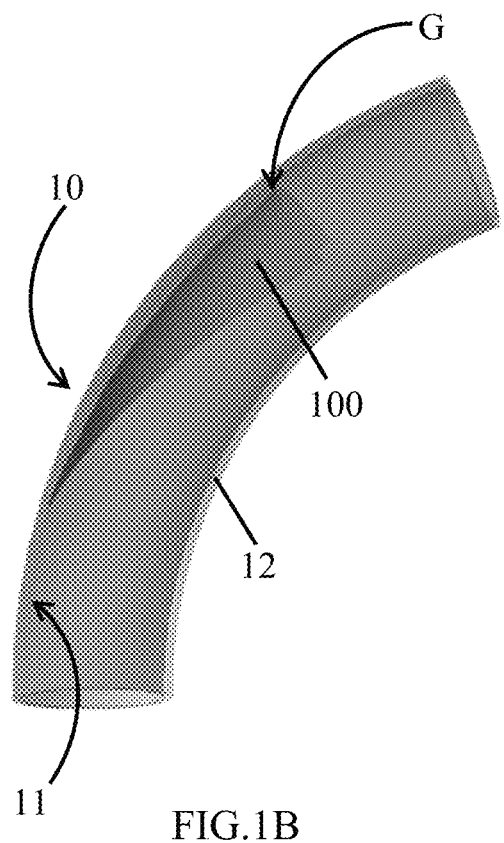
FIG. 1B shows a valved conduit in an open position.

Various embodiments are directed to valved conduits having leaflets that do not contact the wall of the conduit in open position (FIG. 1B). As illustrated in FIG. 1A and FIG. 1B, an exemplary valved conduit encompassed by such embodiments may include a conduit 10 having an inner surface 11 and an outer surface 12. A valve 100 composed of one or more leaflets may be disposed within the conduit 10 and attached to the inner surface 11 of the conduit 10. In open position (FIG. 1B), a sinus gap G separates the inner surface of the conduit 11 from the valve 100.

Figures 2A, 2B:
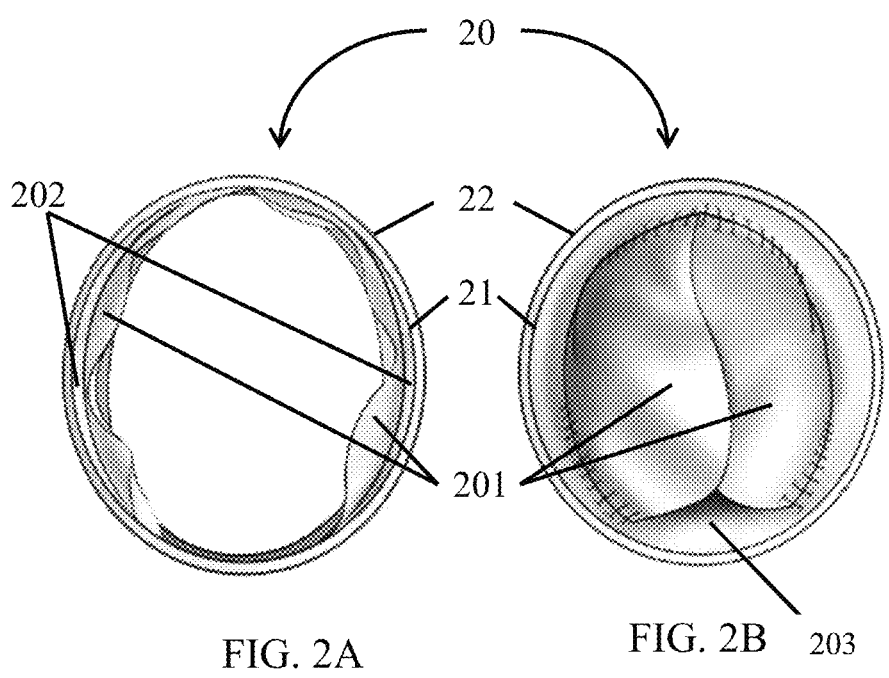
FIG. 2A shows a valved conduit in open position.
FIG. 2B shows a valved conduit in a closed position.

FIG. 2A and FIG. 2B illustrate an interior downstream, cross-sectional view of an exemplary valve encompassed by FIG. 1A and FIG. 1B in an open, FIG. 2A, and closed, FIG. 2B, configuration. In the open (FIG. 2A) configuration, fluid flows through the valve, forcing the fan portion of a leaflet 201 towards the inner surface of the conduit. In the closed configuration (FIG. 2B) the fan portion of the leaflet 201 may form a closure against fluid backflow. FIG. 2A and FIG. 2B shows a conduit 20 having an inner surface 21 and an outer surface 22, and a valve composed of one or more leaflets 201 that are attached to the inner surface 21 of the conduit 20. In open configuration (FIG. 2A), a sinus gap 202 is created between the leaflets 201 and the inner surface 21 of the conduit 20 that allows the leaflets 201 to fully extend without contacting the inner surface 21 of the conduit 20. In embodiments such as those depicted in FIG. 2A and FIG. 2B in which the valve includes two leaflets, at least a portion of the leaflets 201 may overlap along a diameter of the conduit 20 when in closed configuration (FIG. 2B), thereby substantially blocking flow of fluid through the conduit 20. In embodiments in which the valve includes one leaflet, the leaflet may contact the inner surface of the conduit opposite the attachment site of the valve, and in embodiments in which the valve includes three or more leaflets, the leaflets may overlap at a longitudinal axis of the tube.

In some embodiments, a conduit has an attachment point on an inner surface of the conduit. In some embodiments, a valve is attached to the conduit at the attachment point. In some embodiments, the valve is attached to the conduit at one or more attachment points. In some embodiments, the valve is attached to the conduit at a plurality of attachment points. In some embodiments, the vale is attached to the conduit at least one attachment point.

In some embodiments, the valve may be attached to the conduit by suturing, welding, fusion, applying an adhesive, clamping, sintering, heating, chemical welding, static electric, frictional forces, lasering, and combinations thereof. Where the valve is attached to the conduit by welding, fusion, adhesive, sintering, or the like which form a line of attachment rather than a single point, the valve is considered to be attached to the conduit at a plurality of attachment points.

Figure 3A:
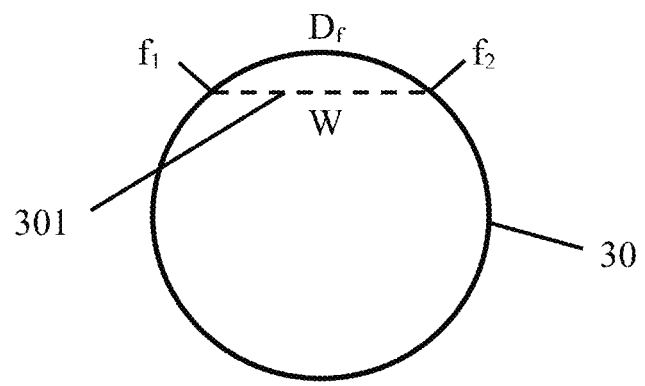
FIG. 3A is a schematic showing the position of a valve in relation to a conduit.
Figure 3B:
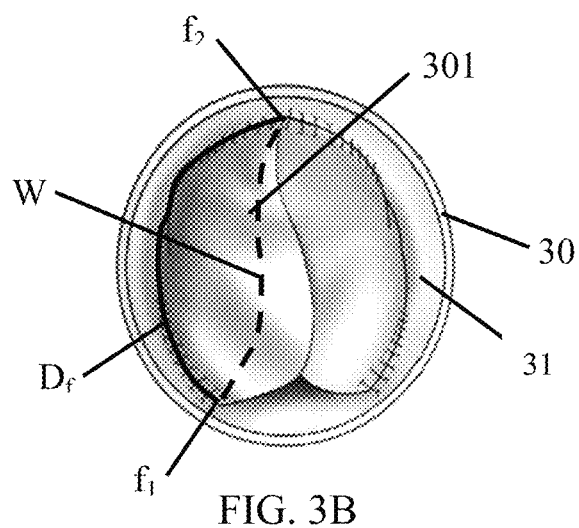
FIG. 3B shows a valved conduit in closed position with the lengths illustrated in FIG. 3A superimposed over the valve components.

The sinus gap 202 between the inner surface 21 of the conduit 20 and the leaflets 201 can be created by any means. For example, in some embodiments, the width W of the leaflets 201 may be shorter than the length of conduit between attachment points, $D_f$. This arrangement is illustrated in FIG. 3A and FIG. 3B. FIG. 3A shows a simple diagram of the valve configuration in which the leaflet 301 of a valve encompassed by the embodiments described above is disposed within a conduit 30 such that the width, W (dashed line), of the leaflet 301 is shorter than the portion of the conduit, $D_f$, between a first attachment point, $f_1$, connecting the leaflet 301 to the inner surface 31 of the conduit 30 and a second attachment point, $f_2$, connecting the leaflet to the inner surface 31 of the conduit 30. This valve configuration is further illustrated in FIG. 3B using the example valve depicted in FIG. 2B. The portion of the conduit, $D_f$, between the first attachment point, $f_1$, and the second attachment point, $f_2$, is longer than the width, W (dashed line), of the leaflet 301.

In some embodiments, a valve gap may be formed by the valve in a closed configuration. Specifically, as shown in FIG. 2B a multi-leaflet valve and at least a portion of a conduit inner surface may be disposed to form a valve gap 203 formed at the intersection of at least a portion of the inner surface of the conduit and a portion of the fan edge.

Figure 4:
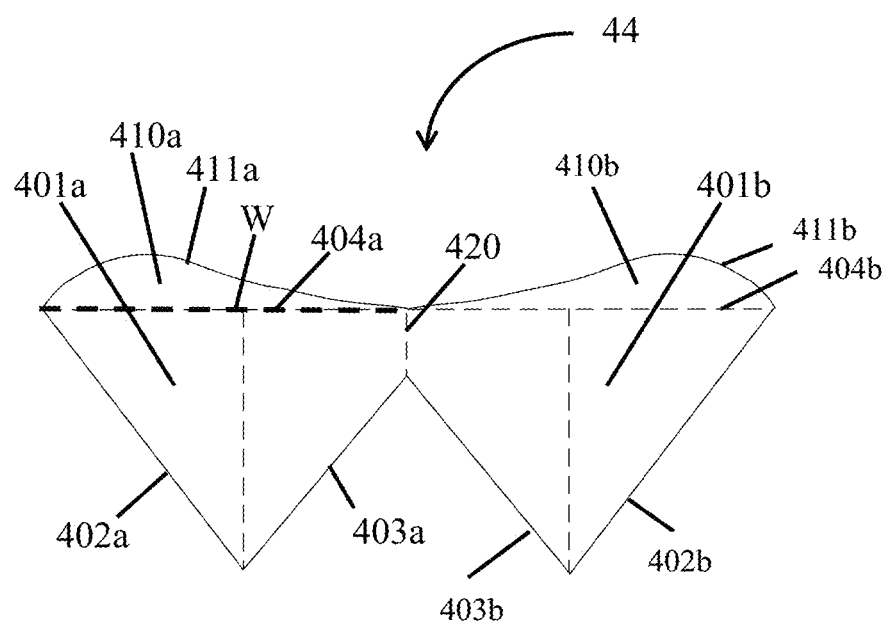
FIG. 4 is an illustration of a leaflet.

FIG. 4 is an illustration of a valve 44 unfolded on single plane with the width, W, of the leaflet illustrated in FIG. 2B identified (dashed line). In some embodiments, the leaflet may have additional features illustrated in FIG. 4. Although FIG. 4 shows a valve 44 configured to create a two leaflets, 401a and 401b, a leaflet for a single leaflet valve or a leaflet for a three or four leaflet valve may include the same elements in a similar configuration.

Each leaflet 401a, 401b may include an outer sinus edge 402a, 402b, an inner sinus edge 403a, 403b, and an open sinus edge 404a, 404b. In embodiments in which the leaflet includes two or more leaflets, the open sinus edge 404a, 404b of each leaflet 401a, 401b may by coextensive as illustrated in FIG. 4. In some embodiments, the valve 44 may have a commissure 420 connecting the first leaflet 401a and the second leaflet 401b. In particular embodiments, the commissure 420 may be a perpendicular intersection connecting each inner sinus edge 403a, 403b with the meeting point of the open sinus edges 404a, 404b, creating a linear connection perpendicular to the open sinus edges 404a, 404b and at an angle to the inner sinus edges 403a, 403b.

In some embodiments, each leaflet 401a, 401b may further include a fan 410a, 410b having a fan edge 411a, 411b extending beyond the open sinus edge 404a, 404b away from the outer sinus edge 401a, 401b and inner sinus edge 402a, 402b. The fan 410a, 410b may allow the leaflets of the valve to contact one another or overlap when the valve is in the closed position (see FIG. 3B) stopping flow of fluid through the valve. The fan 410a, 410b may have any shape, and in certain embodiments, the fan 410a, 410b may have a curved shape with a wide section on one side of the leaflet and a narrow section on the opposite side of the leaflet. In some embodiments, the narrow section of the fan 410a of a first leaflet 401a may connect to a narrow section of the fan 410b of the second leaflet 401b at the commissure 420, and in particular embodiments, the narrow section of the fan 410a of a first leaflet 401a may connect to a narrow section of the second leaflet 401b at the commissure 420 at the connection point of the open sinus edges 404a, 404b.

Figures 5A, 5B:
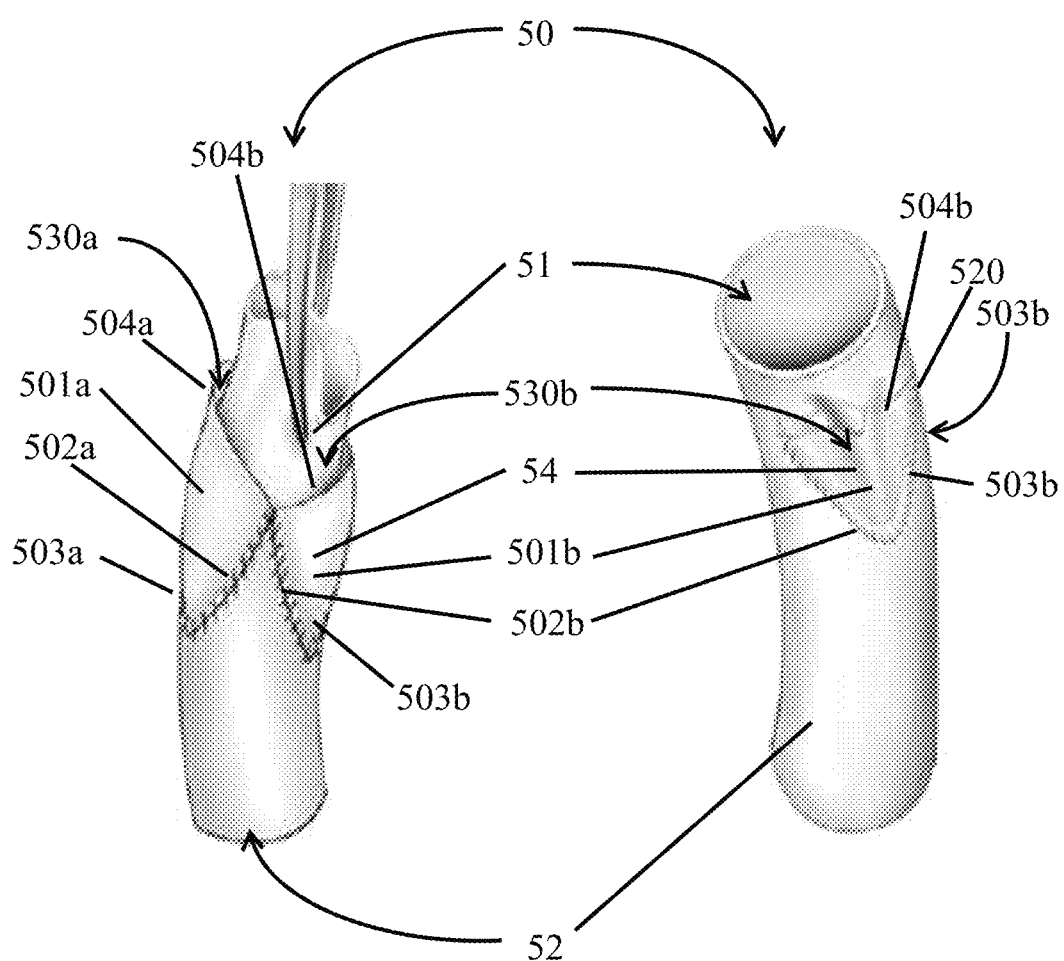
FIG. 5A shows a valved conduit that has been inverted such that the valve is on an outward facing side of the conduit.
FIG. 5B shows a valved conduit with the valve on an inner surface of the conduit.

FIG. 5A and FIG. 5B show a leaflet 54 such as that described in FIG. 4 attached to a conduit 50. In FIG. 5A, the conduit 50 is inverted such that the leaflet 54 is disposed on the outside of the conduit 50, and the conduit 50 is reverted such that the leaflet 54 is inside the conduit 50. Thus, an inner surface 51 is on the outside of the conduit 50 in FIG. 5A, and the inner surface 51 is inside the conduit 50 in FIG. 5B. An outer surface 52 is on the inside of the conduit 50 in FIG. 5A, and the outer surface 52 is outside the conduit 50 in FIG. 5B. The leaflet 54 may be attached to the inner surface 51 of the conduit 50 at the outer sinus edge 502a and 502b and the inner sinus edge 503a and 503b (503a is on the opposite side of the conduit 54). Each of the outer sinus edges 502a, 502b and inner sinus edge 503a, 503b may be attached to the conduit by a substantially fluid impervious connection such as, for example, suturing (as shown), fusion, applying an adhesive, or welding. The commissure 520 may also be attached to the inner surface 51 of the conduit 50 by, for example, suturing (as shown), applying an adhesive, or welding. The open sinus edge 504a, 504b are not attached to the conduit 50, and remain open to fluids flowing through the conduit 50. The opening creates a sinus 530a, 530b between the inner surface 51 of the conduit 50 and each leaflet 501a, 501b, and each open sinus edge 504a, 504b.

Figure 6A:
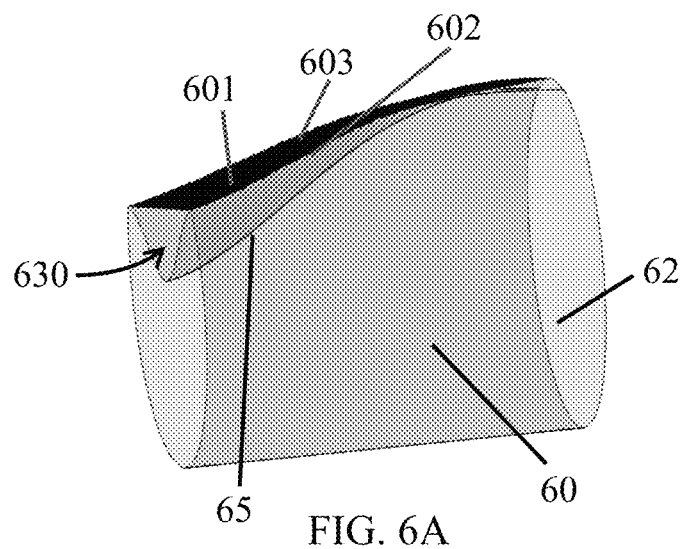
FIG. 6A is a schematic illustrating a tapered dimple created between the leaflet and an inner surface of the conduit in a longitudinal view.
Figure 6B:
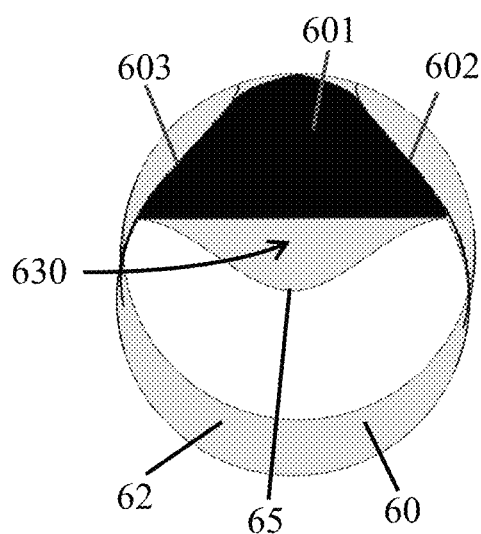
FIG. 6B illustrates a schematic illustrating a tapered dimple created between the leaflet and an inner surface of the conduit in a cross-sectional view.

FIG. 6A and FIG. 6B are a three-dimensional representation of a leaflet 601 (dark shading) on an inverted conduit 60 to show the sinus 630 created by the leaflet 601. FIG. 6A is a longitudinal view and FIG. 6B is a cross-sectional view. As in FIG. 5A, the leaflet 601 is attached to the conduit at the outer sinus edge 602 and inner sinus edge 603 by a substantially fluid impervious connection such as, for example, suturing, applying an adhesive, or welding. A tapered dimple 65 in the conduit 60 underlying the leaflet 601 provides the conduit side of the sinus 630 and allows the valve to achieve the configuration illustrated in FIG. 5B when the conduit 60 is returned to its original shape (i.e. reverted such that the outer surface 62 of the conduit 60 is on an outer surface of the structure). Because the width of the leaflet 601 changes along its length, the degree to which the conduit must bend also changes along the length of the conduit 60.

Figure 7A:
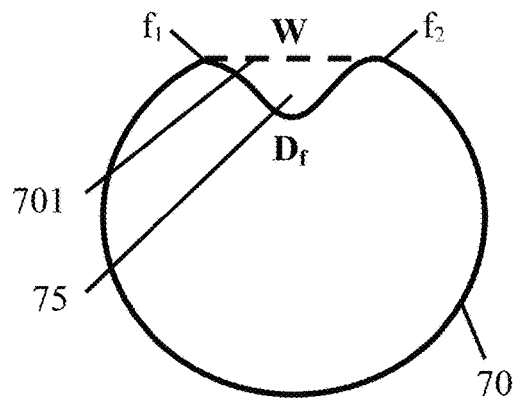
FIG. 7A depicts a valve in an inverted configuration.
Figure 7B:
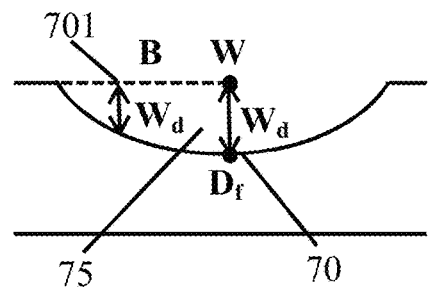
FIG. 7B illustrates a perpendicular cross section of the valve of FIG. 7A.
Figure 7C:
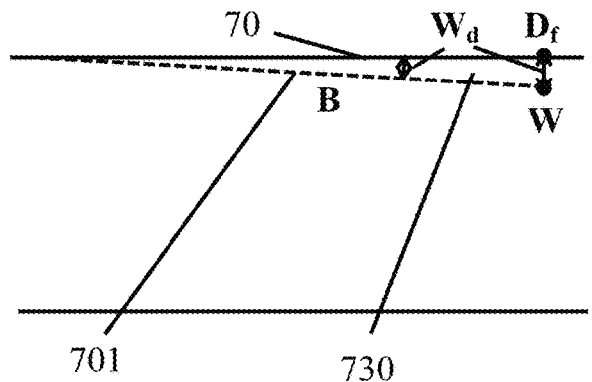
FIG. 7C illustrates a two-dimensional view of the valve in operable configuration where the conduit has been reverted such that the valve is on the inner surface of the conduit.
Figure 7D:
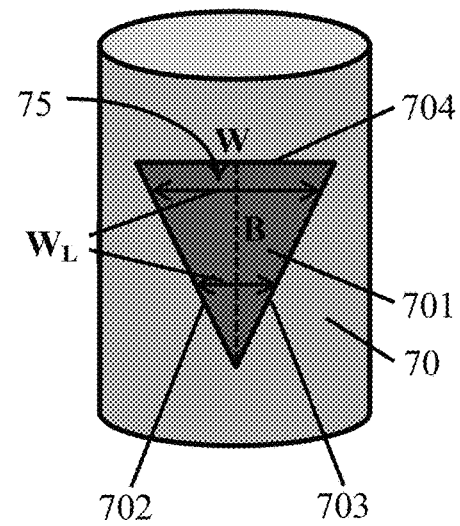
FIG. 7D illustrates a three-dimensional view of the valve in operable configuration where the conduit has been reverted such that the valve is on the inner surface of the conduit.

This arrangement is further illustrated in FIG. 7A, FIG. 7B, FIG. 7C, and FIG. 7D. In FIG. 7A, a valve is in an inverted configuration and shows a leaflet 701 of the valve disposed within a conduit 70 such that the width, W (dashed line), of the leaflet 701 is shorter than the portion of the conduit, $D_f$, between a first attachment point, $f_1$ and a second attachment point, $f_2$, connecting the leaflet 701 to the inner surface of the conduit 70. FIG. 7B is a perpendicular cross section of the valve of FIG. 7A illustrating the tapered dimple 75. B is the length of the leaflet 701. $W_d$ depth of the dimple 75, i.e. the depth of the gap between the leaflet 701 and the conduit 70, which, as illustrated varies with B from the open edge 704 of the leaflet 701 to a point where the outer sinus edge 702 and the inner sinus edge 703 meet (see FIG. 7D). FIG. 7C and FIG. 7D show the valve in operable configuration where the conduit has been reverted such that the valve is on the inner surface of the conduit 70 and conduit 70 has retained its cylindrical shape. The leaflet 701, which has an open edge 704 width, W, that is less than the circumference of the conduit 70 between attachment points may be suspended below the inner surface of the conduit 70 by a depth, $W_d$, which varies with the length, B, of the leaflet 701 creating a sinus 730. With reference to FIG. 7D, in some embodiments, the leaflet 701 may have a substantially triangular shape. Therefore, the leaflet width, W, may also vary with the length, B, of the leaflet 701.

A valve having leaflets as described and discussed above may reduce the contact of the leaflets and, in some embodiments, fans attached to the open sinus edge, with the inner surface of the conduit when the valve is in open configuration. Reduced contact with the inner surface of the conduit decreases the likelihood that the valve will stick in open configuration and may also reduce wear on the leaflet over many cycles. Thus, the valves of various embodiments may provide improved long term use when implanted as part of a medical device. For example, in some embodiments, the valves described above may be used as a shunt for connecting of the right ventricle to the pulmonary artery following a Norwood operation, as frequently performed for the treatment of single-functional-ventricle-disorders such as Hypoplastic Left Heart Syndrome. In other embodiments, the valves described above may be used for the correction or reconstruction of the right ventricle outflow tract (RVOT) for congenital heart disorders such as tetralogy of Fallot, Truncus Arterious, DextroTransposition of the Great Arteries, Pulmonary Atresia of Intact Ventricular Septum, or Aortic Valvular Disease. In still other embodiments, the valves described above may be incorporated into a stent and deployed as artificial valves in adult and pediatric patients.

The conduit 10, 20, 30, 50, 60, 70, and 1101 of various embodiments, and the valve 100, 44, 1102 or leaflet 201, 301, 54, 601, 701, 801 may be constructed from a material. In some embodiments, the material comprises any biocompatible and hemocompatible polymer. In some embodiments, the material can be a fluoropolymer. In some embodiments, the material can be a polymer. In some embodiments, the material can be polytetrafluoroethylene, expanded polytetrafluoroethelyne, polyester, polyethylene terephthalate, polydimethylsiloxane, polyurethane, and combinations thereof. In some embodiments, the material may be extruded. In some embodiments, the material may be an extruded fluoropolymer. In some embodiments, the material may be an extruded polymer. In some embodiments, the fluoropolymer can be polytetrafluoroethylene, expanded polytetrafluoroethelyne, and combinations thereof. In some embodiments, the polymer can be polyester, polyethylene terephthalate, polydimethylsiloxane, polyurethane, and combinations thereof. In some embodiments, the material may be a fluoropolymer coated with a bioactive coating. In some embodiments, the material may be surface-modified to include a surface coating or a bioactive material. In some embodiments, the material may be a polymer coated with a bioactive coating. In some embodiments, the material may be surface-modified to include a surface coating or a bioactive material. The surface coating or bioactive material may be an anti-coagulant coating or an anti-coagulant material that promotes biocompatibility such as, for example, coumadin, heparin, a heparin derivative, a Factor Xa inhibitor, a direct thrombin inhibitor, hementin, sintered porous titanium microspheres, a carbon coating, or combinations thereof.

In some embodiments, the material is non-stretchable. In some embodiments, the material is non-stretchable biocompatible and hemocompatible. Non-limiting examples of non-stretchable biocompatible and hemocompatible material that can be used to make the conduits or valve are polytetrafluoroethylene (PTFE), expanded polytetrafluoroethylene (ePTFE), polyethylene terephthalate (PET), polydimethyl siloxane (PDMS), polyethylene (PE), polypropylene (PP), polyesters, polycarbonates, polyvinyl chloride (PVC), hydrogels, and the like. In some embodiments, the biocompatible and hemocompatible material may be a polymer coated with a bioactive coating. In some embodiments, the biocompatible and hemocompatible polymer may be surface-modified to include a bioactive material.

In some embodiments, the conduit, the valve, or the leaflet are made from a layer of the material. In some embodiments, the conduit, the valve, or the leaflet are made from multiple layer of the material. In some embodiments, the conduit, the valve, or the leaflet are made from more than one material. In some embodiments, the conduit, the valve, or the leaflet are made from one or more layers of the material. In some embodiments, the conduit, the valve, or the leaflet are made from at least two layers of the material. In some embodiments, the conduit, the valve, or the leaflet are made from a first layer of a first material and a second layer of a second material.

The conduit 10, 20, 30, 50, 60, 70, and 1101 described herein may generally be flexible, and the size of the conduit of various embodiments may vary depending on the intended use of the valve. In some embodiments, the conduit may have a diameter in a range of about 40 mm to about 15 mm, about 25 mm to about 2 mm, about 20 mm to about 2 mm, about 15 mm to about 2 mm, about 10 mm to about 2 mm, about 8 mm to about 3 mm, about 5 mm to about 3 mm, or any range or individual diameter encompassed by these example ranges. In other embodiments, the conduit may have a diameter in a range of about 40 mm to about 15 mm, about 25 mm to about 5 mm, about 20 mm to about 8 mm, about 15 mm to about 10 mm, or any range or individual diameter encompassed by these example ranges. In some embodiments, the conduit may have a diameter in a range of about 2 mm to about 40 mm, about 2 mm to about 30 mm, about 2 mm to about 20 mm, about 2 mm to about 10 mm, about 2 mm to about 5 mm. In some embodiments, the conduit may have a diameter in a range of about 5 mm to about 40 mm, about 10 mm to about 40 mm, about 20 mm to about 40 mm. In some embodiments, the conduit diameter is 2 mm. In some embodiments, the conduit diameter is 3 mm. In some embodiments, the conduit diameter is 4 mm. In some embodiments, the conduit diameter is 5 mm. In some embodiments, the conduit diameter is 6 mm. In some embodiments, the conduit diameter is 7 mm. In some embodiments, the conduit diameter is 8 mm.

In some embodiment, the conduit may have a thicknesses in a range of about 0.05 mm to about 0.5 mm, about 0.5 mm to about 2.0 mm, about 0.5 mm to about 1.5 mm, or any range or individual thickness encompassed by these example ranges. In some embodiments, the conduit thickness is 0.05 mm. In some embodiments, the conduit thickness is 0.5 mm. In some embodiments, the conduit thickness is 1.5 mm. In some embodiments, the conduit thickness is 2 mm. In some embodiments, the conduit thickness is 1 mm.

In some embodiments, the conduit comprises more than one layer of the material. In some embodiments, the conduit comprises multiple materials. For example, the conduit may comprise a material having a first yield strength and first ultimate tensile strength and may be impregnated with a second material having a second yield strength and/or second ultimate tensile strength. In some embodiments, the conduit may be fabricated from two or more elastic or plastically deformable materials woven together.

In embodiments in which the conduit includes more than one layer of the material, each layer of a multi-layer conduit may be composed of the same material. In other embodiments, each layer of a multi-layer conduit may be composed of a different material. In further embodiments, each layer of a multi-layer conduit may be composed of a material characterized by different mechanical properties. For example, an inner layer of a multi-layer conduit may include a material having a first yield strength and a first ultimate tensile strength and an outer layer that may include a second material having a second yield strength and/or a second ultimate tensile strength. The first yield strength may be greater than, about equal to, or less than the second yield strength. The first ultimate tensile strength may be greater than, about equal to, or less than the second ultimate tensile strength. Alternatively, an inner layer may include an elastic or plastically deformable material and an outer layer may include an inelastic or frangible material.

In some embodiments, the conduit is constructed from one or more layers of a material having a surface porosity. In some embodiments, the surface porosity of one or more layers is about 1%. In some embodiments, the surface porosity of one or more layers is about 2%. In some embodiments, the surface porosity of one or more layers is about 3%. In some embodiments, the surface porosity of one or more layers is about 4%. In some embodiments, the surface porosity of one or more layers is about 5%. In some embodiments, the surface porosity of one or more layers is about 10%. In some embodiments, the surface porosity of one or more layers is about 15%. In some embodiments, the surface porosity of one or more layers is about 20%. In some embodiments, the surface porosity of one or more layers is about 30%. In some embodiments, the surface porosity of one or more layers is about 40%. In some embodiments, the surface porosity of one or more layers is about 50%. In some embodiments, the surface porosity of one or more layers is about 60%. In some embodiments, the surface porosity of one or more layers is about 70%. In some embodiments, the surface porosity of one or more layers is about 80%. In some embodiments, the surface porosity of one or more layers is about 90%. In some embodiments, the surface porosity of one or more layers is less than 20%. In some embodiments, the surface porosity of one or more layers is less than 15%. In some embodiments, the surface porosity of one or more layers is less than 10%. In some embodiments, the surface porosity of one or more layers is less than 5%. In some embodiments, the surface porosity of one or more layers is less than 4%. In some embodiments, the surface porosity of one or more layers is less than 3%. In some embodiments, the surface porosity of one or more layers is less than 2%. In some embodiments, the surface porosity of one or more layers is less than 1%. In some embodiments, the surface porosity of one or more layers is greater than 20%. In some embodiments, the surface porosity of one or more layers is greater than 30%. In some embodiments, the surface porosity of one or more layers is greater than 40%. In some embodiments, the surface porosity of one or more layers is greater than 50%. In some embodiments, the surface porosity of one or more layers is greater than 60%. In some embodiments, the surface porosity of one or more layers is greater than 70%. In some embodiments, the surface porosity of one or more layers is greater than 80%. In some embodiments, the surface porosity of one or more layers is greater than 90%. In some embodiments, the surface porosity of one or more layers is in a range of about 1% to about 20%. In some embodiments, the surface porosity of one or more layers is in a range of about 1% to about 15%. In some embodiments, the surface porosity of one or more layers is in a range of about 1% to about 10%. In some embodiments, the surface porosity of one or more layers is in a range of about 1% to about 5%. In some embodiments, the surface porosity of one or more layers is in a range of about 1% to about 4%. In some embodiments, the surface porosity of one or more layers is in a range of about 1% to about 3%. In some embodiments, the surface porosity of one or more layers is in a range of about 1% to about 2%. In some embodiments, the surface porosity of one or more layers is in a range of about 2% to about 20%. In some embodiments, the surface porosity of one or more layers is in a range of about 3% to about 20%. In some embodiments, the surface porosity of one or more layers is in a range of about 4% to about 20%. In some embodiments, the surface porosity of one or more layers is in a range of about 5% to about 20%. In some embodiments, the surface porosity of one or more layers is in a range of about 10% to about 20%. In some embodiments, the surface porosity of one or more layers is in a range of about 15% to about 20%. In some embodiments, the surface porosity of one or more layers is in a range of about 2% to about 15%. In some embodiments, the surface porosity of one or more layers is in a range of about 3% to about 10%. In some embodiments, the surface porosity of one or more layers is in a range of about 4% to about 10%. In some embodiments, the surface porosity of one or more layers is in a range of about 5% to about 10%. In some embodiments, the surface porosity of one or more layers is in a range of about 5% to about 20%. In some embodiments, the surface porosity of one or more layers is in a range of about 5% to about 15%. In some embodiments, the surface porosity of one or more layers is in a range of about 5% to about 10%. In some embodiments, the surface porosity of one or more layers is in a range of about 20% to about 90%. In some embodiments, the surface porosity of one or more layers is in a range of about 20% to about 80%. In some embodiments, the surface porosity of one or more layers is in a range of about 20% to about 70%. In some embodiments, the surface porosity of one or more layers is in a range of about 20% to about 60%. In some embodiments, the surface porosity of one or more layers is in a range of about 20% to about 50%. In some embodiments, the surface porosity of one or more layers is in a range of about 20% to about 40%. In some embodiments, the surface porosity of one or more layers is in a range of about 20% to about 30%. In some embodiments, the surface porosity of one or more layers is in a range of about 30% to about 90%. In some embodiments, the surface porosity of one or more layers is in a range of about 40% to about 90%. In some embodiments, the surface porosity of one or more layers is in a range of about 50% to about 90%. In some embodiments, the surface porosity of one or more layers is in a range of about 60% to about 90%. In some embodiments, the surface porosity of one or more layers is in a range of about 70% to about 90%. In some embodiments, the surface porosity of one or more layers is in a range of about 80% to about 90%. In some embodiments, the surface porosity of one or more layers is in a range of about 30% to about 80%. In some embodiments, the surface porosity of one or more layers is in a range of about 30% to about 70%. In some embodiments, the surface porosity of one or more layers is in a range of about 30% to about 60%. In some embodiments, the surface porosity of one or more layers is in a range of about 30% to about 50%. In some embodiments, the surface porosity of one or more layers is in a range of about 30% to about 40%. In some embodiments, the surface porosity of one or more layers is in a range of about 40% to about 80%. In some embodiments, the surface porosity of one or more layers is in a range of about 50% to about 80%. In some embodiments, the surface porosity of one or more layers is in a range of about 60% to about 80%. In some embodiments, the surface porosity of one or more layers is in a range of about 70% to about 80%. In some embodiments, the surface porosity of one or more layers is in a range of about 40% to about 70%. In some embodiments, the surface porosity is in a range of about 40% to about 60%. In some embodiments, the surface porosity of one or more layers is in a range of about 40% to about 50%. In some embodiments, the surface porosity of one or more layers is in a range of about 50% to about 70%. In some embodiments, the surface porosity of one or more layers is in a range of about 60% to about 70%.

Conduits composed of multiple layers may have expansion capabilities depending on the material properties of the multiple layers. In some embodiments, a conduit comprising a biodegradable outer layer and an elastic or plastically deformable inner layer may be expanded due to the force of a fluid flowing therein but only after the outer layer has degraded. In some embodiments, a conduit having an inelastic or frangible outer layer and an elastic or plastically deformable inner layer may remain in an unexpanded state until sufficient force, for example, supplied by an inserted expansion device, is applied internally to rupture the outer layer and thus permit the inner layer to expand.

In some embodiments, the conduit materials, formulations, and/or mechanical properties may be constant over the longitudinal dimension of the conduit. In some embodiments, the conduit materials, formulations, and/or mechanical properties of the conduit may vary along the length or any partial length of the conduit. Conduits having multiple branches may have mechanical properties that differ between the branches and/or a main cylindrical tube of the conduit.

In certain embodiments, the conduits described above may include additional components. In some embodiments, the conduit may include a stent that is attached to or encapsulated by the material of the conduit, or an inner layer may include a stent while an outer layer may include an elastic or plastically deformable material. In some embodiments, a conduit may be composed of a biodegradable outer layer and an elastic or plastically deformable inner layer. In some further examples, a multi-layer conduit may include a first inner layer comprising a woven material and a second outer layer comprising a woven material. It may be understood that the woven material composing the inner layer may be the same as the woven material composing the outer layer. Alternatively, the woven material composing the inner layer may differ from the woven material composing the outer layer.

In some embodiments, the conduit may comprise a valve. In some embodiments, the valved conduit may include a conduit having a first conduit layer having an inner surface in physical communication with an outer surface of a second conduit layer and the valve is disposed within the second conduit layer. As one example of such a multi-layer valved conduit, the first conduit layer may be composed of a first plastically deformable material having a yield strength of about 0.1 MPa to about 4 MPa, and the second conduit layer may be composed of the same plastically deformable material as the first layer. In an alternative example, the multi-layer valved conduit may be composed of a first conduit layer having a first plastically deformable material having a yield strength of about 0.1 MPa to about 4 MPa, and a second conduit layer composed of a second material that may differ from the first material. In still another example, the valved conduit may have a first conduit layer composed of a woven material, a second conduit layer composed of a woven material, or both the first conduit layer and the second conduit layer may each be composed of a woven material. In some embodiments of the multi-layer valved conduit, the first conduit layer may be biodegradable. In some alternative embodiments of a multi-layer valved conduit, the first conduit layer may include a non-plastically deformable material. In yet another embodiment, the multi-layer valved conduit may include a stent as part of the second conduit layer.

In some embodiments, the conduit has a yield strength. In some embodiments, the yield strength is about 0.1 MPa to about 4 MPa. In some embodiments, the yield strength is about 0.2 MPa to about 4 MPa. In some embodiments, the yield strength is about 0.3 MPa to about 4 MPa. In some embodiments, the yield strength is about 0.4 MPa to about 4 MPa. In some embodiments, the yield strength is about 0.5 MPa to about 4 MPa. In some embodiments, the yield strength is about 0.6 MPa to about 4 MPa. In some embodiments, the yield strength is about 0.7 MPa to about 4 MPa. In some embodiments, the yield strength is about 0.8 MPa to about 4 MPa. In some embodiments, the yield strength is about 0.9 MPa to about 4 MPa. In some embodiments, the yield strength is about 1 MPa to about 4 MPa. In some embodiments, the yield strength is about 0.1 MPa to about 0.2 MPa. In some embodiments, the yield strength is about 0.1 MPa to about 0.3 MPa. In some embodiments, the yield strength is about 0.1 MPa to about 0.4 MPa. In some embodiments, the yield strength is about 0.1 MPa to about 0.5 MPa. In some embodiments, the yield strength is about 0.1 MPa to about 0.6 MPa. In some embodiments, the yield strength is about 0.1 MPa to about 0.7 MPa. In some embodiments, the yield strength is about 0.1 MPa to about 0.8 MPa. In some embodiments, the yield strength is about 0.1 MPa to about 0.9 MPa. In some embodiments, the yield strength is about 0.1 MPa to about 1 MPa. In some embodiments, the yield strength is about 0.1 MPa to about 12 MPa. In some embodiments, the yield strength is about 0.1 MPa to about 11 MPa. In some embodiments, the yield strength is about 0.1 MPa to about 10 MPa. In some embodiments, the yield strength is about 0.1 MPa to about 9 MPa. In some embodiments, the yield strength is about 0.1 MPa to about 8 MPa. In some embodiments, the yield strength is about 0.1 MPa to about 7 MPa. In some embodiments, the yield strength is about 0.1 MPa to about 6 MPa. In some embodiments, the yield strength is about 0.1 MPa to about 5 MPa. In some embodiments, the yield strength is about 0.2 MPa to about 12 MPa. In some embodiments, the yield strength is about 0.2 MPa to about 11 MPa. In some embodiments, the yield strength is about 0.2 MPa to about 10 MPa. In some embodiments, the yield strength is about 0.2 MPa to about 9 MPa. In some embodiments, the yield strength is about 0.2 MPa to about 8 MPa. In some embodiments, the yield strength is about 0.2 MPa to about 7 MPa. In some embodiments, the yield strength is about 0.2 MPa to about 6 MPa. In some embodiments, the yield strength is about 0.2 MPa to about 5 MPa. In some embodiments, the yield strength is about 0.3 MPa to about 12 MPa. In some embodiments, the yield strength is about 0.3 MPa to about 11 MPa. In some embodiments, the yield strength is about 0.3 MPa to about 10 MPa. In some embodiments, the yield strength is about 0.3 MPa to about 9 MPa. In some embodiments, the yield strength is about 0.3 MPa to about 8 MPa. In some embodiments, the yield strength is about 0.3 MPa to about 7 MPa. In some embodiments, the yield strength is about 0.3 MPa to about 6 MPa. In some embodiments, the yield strength is about 0.3 MPa to about 5 MPa. In some embodiments, the yield strength is about 0.4 MPa to about 12 MPa. In some embodiments, the yield strength is about 0.4 MPa to about 11 MPa. In some embodiments, the yield strength is about 0.4 MPa to about 10 MPa. In some embodiments, the yield strength is about 0.4 MPa to about 9 MPa. In some embodiments, the yield strength is about 0.4 MPa to about 8 MPa. In some embodiments, the yield strength is about 0.4 MPa to about 7 MPa. In some embodiments, the yield strength is about 0.4 MPa to about 6 MPa. In some embodiments, the yield strength is about 0.4 MPa to about 5 MPa. In some embodiments, the yield strength is about 0.5 MPa to about 12 MPa. In some embodiments, the yield strength is about 0.5 MPa to about 11 MPa. In some embodiments, the yield strength is about 0.5 MPa to about 10 MPa. In some embodiments, the yield strength is about 0.5 MPa to about 9 MPa. In some embodiments, the yield strength is about 0.5 MPa to about 8 MPa. In some embodiments, the yield strength is about 0.5 MPa to about 7 MPa. In some embodiments, the yield strength is about 0.5 MPa to about 6 MPa. In some embodiments, the yield strength is about 0.5 MPa to about 5 MPa. In some embodiments, the yield strength is about 0.6 MPa to about 12 MPa. In some embodiments, the yield strength is about 0.6 MPa to about 11 MPa. In some embodiments, the yield strength is about 0.6 MPa to about 10 MPa. In some embodiments, the yield strength is about 0.6 MPa to about 9 MPa. In some embodiments, the yield strength is about 0.6 MPa to about 8 MPa. In some embodiments, the yield strength is about 0.6 MPa to about 7 MPa. In some embodiments, the yield strength is about 0.6 MPa to about 6 MPa. In some embodiments, the yield strength is about 0.6 MPa to about 5 MPa. In some embodiments, the yield strength is about 0.7 MPa to about 12 MPa. In some embodiments, the yield strength is about 0.7 MPa to about 11 MPa. In some embodiments, the yield strength is about 0.7 MPa to about 10 MPa. In some embodiments, the yield strength is about 0.7 MPa to about 9 MPa. In some embodiments, the yield strength is about 0.7 MPa to about 8 MPa. In some embodiments, the yield strength is about 0.7 MPa to about 7 MPa. In some embodiments, the yield strength is about 0.7 MPa to about 6 MPa. In some embodiments, the yield strength is about 0.7 MPa to about 5 MPa. In some embodiments, the yield strength is about 0.8 MPa to about 12 MPa. In some embodiments, the yield strength is about 0.8 MPa to about 11 MPa. In some embodiments, the yield strength is about 0.8 MPa to about 10 MPa. In some embodiments, the yield strength is about 0.8 MPa to about 9 MPa. In some embodiments, the yield strength is about 0.8 MPa to about 8 MPa. In some embodiments, the yield strength is about 0.8 MPa to about 7 MPa. In some embodiments, the yield strength is about 0.8 MPa to about 6 MPa. In some embodiments, the yield strength is about 0.8 MPa to about 5 MPa. In some embodiments, the yield strength is about 0.9 MPa to about 12 MPa. In some embodiments, the yield strength is about 0.9 MPa to about 11 MPa. In some embodiments, the yield strength is about 0.9 MPa to about 10 MPa. In some embodiments, the yield strength is about 0.9 MPa to about 9 MPa. In some embodiments, the yield strength is about 0.9 MPa to about 8 MPa. In some embodiments, the yield strength is about 0.9 MPa to about 7 MPa. In some embodiments, the yield strength is about 0.9 MPa to about 6 MPa. In some embodiments, the yield strength is about 0.9 MPa to about 5 MPa. In some embodiments, the yield strength is about 1 MPa to about 12 MPa. In some embodiments, the yield strength is about 1 MPa to about 11 MPa. In some embodiments, the yield strength is about 1 MPa to about 10 MPa. In some embodiments, the yield strength is about 1 MPa to about 9 MPa. In some embodiments, the yield strength is about 1 MPa to about 8 MPa. In some embodiments, the yield strength is about 1 MPa to about 7 MPa. In some embodiments, the yield strength is about 1 MPa to about 6 MPa. In some embodiments, the yield strength is about 1 MPa to about 5 MPa. In some embodiments, the yield strength is about 2 MPa to about 12 MPa. In some embodiments, the yield strength is about 2 MPa to about 11 MPa. In some embodiments, the yield strength is about 2 MPa to about 10 MPa. In some embodiments, the yield strength is about 2 MPa to about 9 MPa. In some embodiments, the yield strength is about 2 MPa to about 8 MPa. In some embodiments, the yield strength is about 2 MPa to about 7 MPa. In some embodiments, the yield strength is about 2 MPa to about 6 MPa. In some embodiments, the yield strength is about 2 MPa to about 5 MPa. In some embodiments, the yield strength is about 3 MPa to about 12 MPa. In some embodiments, the yield strength is about 3 MPa to about 11 MPa. In some embodiments, the yield strength is about 3 MPa to about 10 MPa. In some embodiments, the yield strength is about 3 MPa to about 9 MPa. In some embodiments, the yield strength is about 3 MPa to about 8 MPa. In some embodiments, the yield strength is about 3 MPa to about 7 MPa. In some embodiments, the yield strength is about 3 MPa to about 6 MPa. In some embodiments, the yield strength is about 3 MPa to about 5 MPa. In some embodiments, the yield strength is about 4 MPa to about 12 MPa. In some embodiments, the yield strength is about 4 MPa to about 11 MPa. In some embodiments, the yield strength is about 4 MPa to about 10 MPa. In some embodiments, the yield strength is about 4 MPa to about 9 MPa. In some embodiments, the yield strength is about 4 MPa to about 8 MPa. In some embodiments, the yield strength is about 4 MPa to about 7 MPa. In some embodiments, the yield strength is about 4 MPa to about 6 MPa. In some embodiments, the yield strength is about 4 MPa to about 5 MPa. In some embodiments, the yield strength is about 5 MPa to about 12 MPa. In some embodiments, the yield strength is about 5 MPa to about 11 MPa. In some embodiments, the yield strength is about 5 MPa to about 10 MPa. In some embodiments, the yield strength is about 5 MPa to about 9 MPa. In some embodiments, the yield strength is about 5 MPa to about 8 MPa. In some embodiments, the yield strength is about 5 MPa to about 7 MPa. In some embodiments, the yield strength is about 5 MPa to about 6 MPa. In some embodiments, the yield strength is about 6 MPa to about 12 MPa. In some embodiments, the yield strength is about 6 MPa to about 11 MPa. In some embodiments, the yield strength is about 6 MPa to about 10 MPa. In some embodiments, the yield strength is about 6 MPa to about 9 MPa. In some embodiments, the yield strength is about 6 MPa to about 8 MPa. In some embodiments, the yield strength is about 6 MPa to about 7 MPa. In some embodiments, the yield strength is about 7 MPa to about 12 MPa. In some embodiments, the yield strength is about 7 MPa to about 11 MPa. In some embodiments, the yield strength is about 7 MPa to about 10 MPa. In some embodiments, the yield strength is about 7 MPa to about 9 MPa. In some embodiments, the yield strength is about 7 MPa to about 8 MPa. In some embodiments, the yield strength is about 8 MPa to about 12 MPa. In some embodiments, the yield strength is about 8 MPa to about 11 MPa. In some embodiments, the yield strength is about 8 MPa to about 10 MPa. In some embodiments, the yield strength is about 8 MPa to about 9 MPa. In some embodiments, the yield strength is about 9 MPa to about 12 MPa. In some embodiments, the yield strength is about 9 MPa to about 11 MPa. In some embodiments, the yield strength is about 9 MPa to about 10 MPa. In some embodiments, the yield strength is about 10 MPa to about 12 MPa. In some embodiments, the yield strength is about 10 MPa to about 11 MPa. In some embodiments, the yield strength is about 0.1 MPa. In some embodiments, the yield strength is about 0.2 MPa. In some embodiments, the yield strength is about 0.3 MPa. In some embodiments, the yield strength is about 0.4 MPa. In some embodiments, the yield strength is about 0.5 MPa. In some embodiments, the yield strength is about 0.6 MPa. In some embodiments, the yield strength is about 0.7 MPa. In some embodiments, the yield strength is about 0.8 MPa. In some embodiments, the yield strength is about 0.9 MPa. In some embodiments, the yield strength is about 1 MPa. In some embodiments, the yield strength is about 2 MPa. In some embodiments, the yield strength is about 3 MPa. In some embodiments, the yield strength is about 4 MPa. In some embodiments, the yield strength is about 5 MPa. In some embodiments, the yield strength is about 6 MPa. In some embodiments, the yield strength is about 7 MPa. In some embodiments, the yield strength is about 8 MPa. In some embodiments, the yield strength is about 9 MPa. In some embodiments, the yield strength is about 10 MPa. In some embodiments, the yield strength is about 11 MPa. In some embodiments, the yield strength is about 12 MPa.

The valve 100, 44, 1102 or leaflet 201, 301, 54, 601, 701, and 801 may have a thickness of about 0.05 mm to about 0.3 mm in various embodiments, and this thickness may vary within the valve. In some embodiments, the valve may comprise a material having a a thickness or total thickness of about 0.05 mm to about 0.3 mm, about 0.1 mm to about 0.3 mm, about 0.15 mm to about 0.3 mm, about 0.2 mm to about 0.3 mm, about 0.25 mm to about 0.3 mm, about 0.05 mm to about 0.25 mm, about 0.1 mm to about 0.25 mm, about 0.2 mm to about 0.25 mm, about 0.05 mm to about 0.2 mm, about 0.1 mm to about 0.2 mm, about 0.15 mm to about 0.2 mm, or a value within any of these range. For example, in some embodiments, the sinus portion of the leaflet may have a greater thickness than the fan portion or the fan portion may have a greater thickness than the sinus portion of the leaflet. The thickness of the valve may be selected to provide sufficient flexibility to allow the valve to obtain the open and closed configurations under the pressure of the flow of fluid through the conduit. The dimensions of each leaflet may vary depending on the diameter of the conduit and the number of leaflets making up the valve. For example with reference to FIG. 7D, in various embodiments, ratio the length, B, of a leaflet 701, and the width, W, leaflet may be about 0.2 to about 2, about 0.3 to about 2, about 0.4 to about 2, about 0.5 to about 2, about 0.6 to about 2, about 0.75 to about 2, about 1 to about 2, about 1 to about 1, or any ratio therebetween or any ratio encompassed by these example ratios. In some embodiments, the ratio of the width of the leaflet to a portion of the conduit circumference between the attachment points may be about 0.63 to about 1, about 0.7 to about 1, about 0.5 to about 1, or any ratio therebetween or any ratio encompassed by these example ratios. The ratio of the width, W, the leaflet 701 to the diameter of the conduit may be about 0.02 to about 3, about 0.05 to about 3, about 0.08 to about 3, about 0.1 to about 3, about 0.2 to about 3, about 0.5 to about 3, about 1 to about 3, about 0.9 to about 1.7, or any ratio therebetween or any ratio encompassed by these example ratios. In embodiments, including a commissure 420 (FIG. 4) i.e. valves having more than one leaflet, the ratio between a length of the commissure 420 and the width, W, of the leaflet 401, may be about 0.05 to about 2, about 0.1 to about 2, about 0.2 to about 2, about 0.3 to about 2, about 0.5 to about 2, or any ratio therebetween or any ratio encompassed by these example ratios. The ratio of the inner sinus edge 703 the leaflet 701 to the width, W, of the leaflet 701 may be about 0.2 to about 2.5, about 0.3 to about 2.5, about 0.4 to about 2.5, about 0.5 to about 2.5, about 0.6 to about 2.5, about 0.75 to about 2.5, about 1 to about 2.5, about 1 to about 1, or any ratio therebetween or any ratio encompassed by these example ratios.

In various such embodiments, the width, W, of the leaflet 701 may be about 1 mm to about 10 mm, about 2 mm to about 7 mm, about 2 mm to about 5 mm, about 20 mm to about 40 mm, about 10 mm to about 30 mm, or any individual width or range encompassed by these example widths. The length, B, of the leaflet 701 may be about 5 mm to about 40 mm, about 5 mm to about 30 mm, about 8 mm to about 25 mm, about 10 mm to about 20 mm, or any individual length, B, or range encompassed by these example lengths. The length of the inner sinus edge 703 about outer sinus edge 704 may each, individually, be about 5 mm to about 45 mm, about 5 mm to about 35 mm, about 8 mm to about 30 mm, about 10 mm to about 20 mm, or any individual length or range encompassed by these example lengths. In some embodiments, multiple leaflet valves may have no commissure, and in other embodiments, multiple leaflet valves may have a commissure having a length of about 0.05 mm, about 0.1 mm, about 0.2 mm, about 0.3 mm, about 0.5 mm, about 0.8 mm, about 1.0 mm, about 1.5 mm, about 2.0 mm, about 4.0 mm, about 6.0 mm, about 8.0 mm, about 10.0 mm, about 12.0 mm, or any range encompassing these example lengths.

Figure 10:
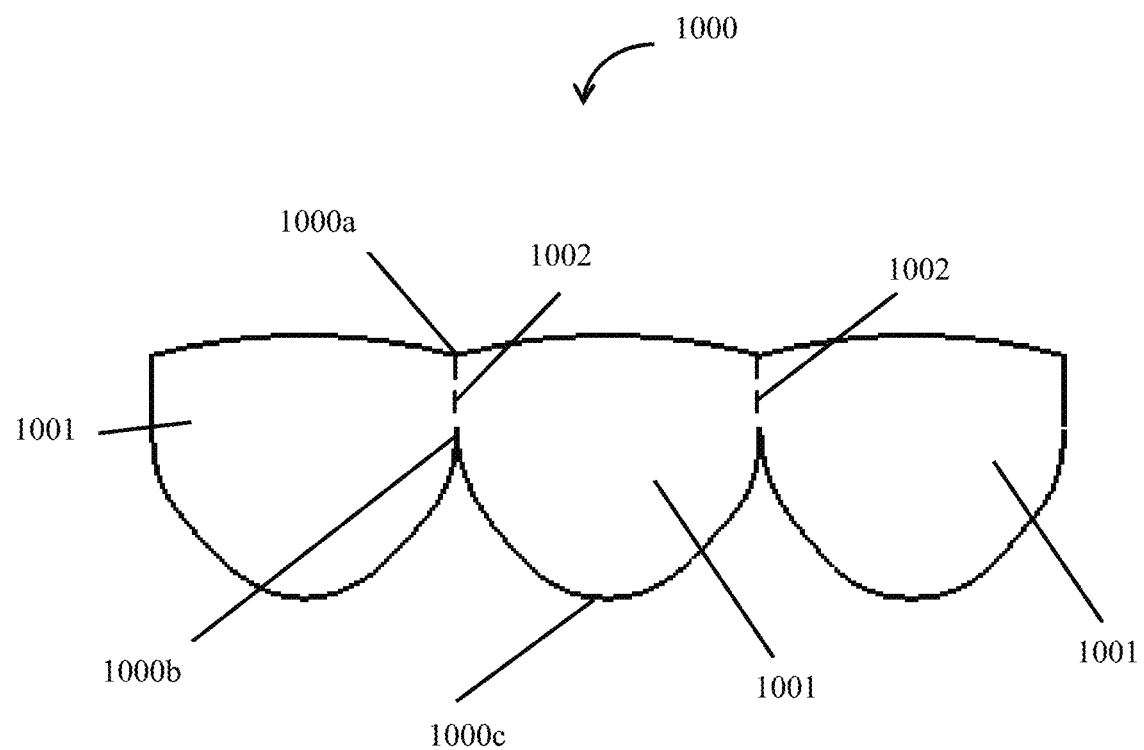
FIG. 10 illustrates a schematic design of a leaflet made from a non-stretchable material, according to an embodiment.

Although FIG. 2A, FIG. 2B, FIG. 3A, FIG. 3B, FIG. 4, FIG. 5A, FIG. 5B, FIG. 6A, FIG. 6B, FIG. 7A, FIG. 7B, FIG. 7C, and FIG. 7D illustrate valve structures composed of one or two leaflets, the valve of other embodiments may be composed of any number of leaflets. For example, embodiments include a valve having three and four leaflets in which each leaflet has an inner and outer sinus edge, a fan edge, a fan, and a commissure between each neighboring leaflet. For example, a three-leaflet valve may include two commissures: one commissure between a first leaflet and a second leaflet, and a second commissure between the second leaflet and a third leaflet. Equivalent metrics to those described above can be used to describe each leaflet of a multi-leaflet valve. The valve may incorporate a closure formed by the juxtaposition, proximity, and/or overlap of three or four fan structures. The mutual disposition of some portions of the three or four fan edges along with the inner surface of the conduit may result in a gap similar to the gap area described above. In some embodiments, the entire valve along with the leaflets are made from a single piece of biocompatible material as shown in FIG. 10.

The valve described herein is not limited to a particular utility. For example, in some embodiments, the valve described herein can be used as heart valves for use in cardiac, coronary or vascular procedures, which may be composed of one or more leaflets. The term may encompass, as non-limiting examples, a heart valve single leaflet having a single heart valve leaflet, or a heart valve multi-leaflet having more than one heart valve leaflet. Each heart valve leaflet may include a sinus edge, a fan edge, a sinus structure, and a fan structure, and additional structural components such as, without limitation, a conduit (which may be tube-like, stent-like, or multi-layered such as a tube within a stent) and one or more conduit sinus structures. The term may encompass a single leaflet valve having a valve single leaflet structure, or a multi-leaflet valve structure composed of either multiple valve single leaflet structures or a valve multi-leaflet structure.

In some embodiments, leaflets are constructed from at least one layer of the material with each layer having a plurality of pores, with each individual pore being defined by a pore area. In some embodiments, the plurality of pores may be disconnected, such that there is limited communication between the pores, separated by a solid node of material. In some embodiments, the plurality of pores have the same pore area. In some embodiments, the pluarality of pores have a different pore area. In some embodiments, the pore area is about 1 square micron. In some embodiments, the pore area is about 0.5 square micron. In some embodiments, the pore area is about 0.25 square micron. In some embodiments, the pore area is about 0.1 square micron. In some embodiments, the pore area is less than 1 square micron. In some embodiments, the pore area is less than 0.5 square micron. In some embodiments, the pore area is less than 0.25 square micron. In some embodiments, the pore area is less than 0.1 square micron. In some embodiments, the pore area is up to 1 square micron. In some embodiments, the pore area is up to 0.5 square micron. In some embodiments, the pore area is up to 0.25 square micron. In some embodiments, the pore area is up to 0.1 square micron. In some embodiments, the pore area is in a range of about 0.05 square micron to about 1 square micron. In some embodiments, the pore area is in a range of about 0.1 square micron to about 1 square micron. In some embodiments, the pore area is in a range of about 0.25 square micron to about 1 square micron. In some embodiments, the pore area is in a range of about 0.5 square micron to about 1 square micron. In some embodiments, the pore area is in a range of about 0.05 square micron to about 0.5 square micron. In some embodiments, the pore area is in a range of about 0.05 square micron to about 0.25 square micron. In some embodiments, the pore area is in a range of about 0.05 square micron to about 0.1 square micron.

In some embodiments, leaflets are constructed from at least one layer of the material with a layer having a plurality of pores, with each individual pore being defined by a pore area. In some embodiments, the plurality of pores may be disconnected, such that there is limited communication between the pores, separated by a solid node of material. In some embodiments, the plurality of pores have a different pore area. In some embodiments, the plurality of pores having a different pore area are defined by an average pore area for the material. The average pore area is calculated by adding the pore area of the plurality of pores and dividing by the total number of pores. In some embodiments, the average pore area is about 1 square micron. In some embodiments, the average pore area is about 0.5 square micron. In some embodiments, the average pore area is about 0.25 square micron. In some embodiments, the average pore area is about 0.1 square micron. In some embodiments, the average pore area is less than 1 square micron. In some embodiments, the average pore area is less than 0.5 square micron. In some embodiments, the average pore area is less than 0.25 square micron. In some embodiments, the average pore area is less than 0.1 square micron. In some embodiments, the average pore area is up to 1 square micron. In some embodiments, the average pore area is up to 0.5 square micron. In some embodiments, the average pore area is up to 0.25 square micron. In some embodiments, the average pore area is up to 0.1 square micron. In some embodiments, the average pore area is in a range of about 0.05 square micron to about 1 square micron. In some embodiments, the average pore area is in a range of about 0.1 square micron to about 1 square micron. In some embodiments, the average pore area is in a range of about 0.25 square micron to about 1 square micron. In some embodiments, the average pore area is in a range of about 0.5 square micron to about 1 square micron. In some embodiments, the average pore area is in a range of about 0.05 square micron to about 0.5 square micron. In some embodiments, the average pore area is in a range of about 0.05 square micron to about 0.25 square micron. In some embodiments, the average pore area is in a range of about 0.05 square micron to about 0.1 square micron.

In some embodiments, leaflets are constructed from at least one layer of a material having a plurality of pores, with each individual pore being defined by a pore diameter. In some embodiments, the plurality of pores may be disconnected, such that there is limited communication between the pores, separated by a solid node of material. In some embodiments, the plurality of pores have the same pore diameter. In some embodiments, the pluarality of pores have a different pore diameter. In some embodiments, the pore diameter is about 1 micron. In some embodiments, the pore diameter is about 0.5 micron. In some embodiments, the pore diameter is about 0.25 micron. In some embodiments, the pore diameter is about 0.1 micron. In some embodiments, the pore diameter is less than 1 micron. In some embodiments, the pore diameter is less than 0.5 micron. In some embodiments, the pore diameter is less than 0.25 micron. In some embodiments, the pore diameter is less than 0.1 micron. In some embodiments, the pore diameter is up to 1 micron. In some embodiments, the pore diameter is up to 0.5 micron. In some embodiments, the pore diameter is up to 0.25 micron. In some embodiments, the pore diameter is up to 0.1 micron. In some embodiments, the pore diameter is in a range of about 0.05 micron to about 1 micron. In some embodiments, the pore diameter is in a range of about 0.1 micron to about 1 micron. In some embodiments, the pore diameter is in a range of about 0.25 micron to about 1 micron. In some embodiments, the pore diameter is in a range of about 0.5 micron to about 1 micron. In some embodiments, the pore diameter is in a range of about 0.05 micron to about 0.5 micron. In some embodiments, the pore diameter is in a range of about 0.05 micron to about 0.25 micron. In some embodiments, the pore diameter is in a range of about 0.05 micron to about 0.1 micron.

In some embodiments, leaflets are constructed from at least one layer of a material having a plurality of pores, with each individual pore being defined by a pore diameter. In some embodiments, the plurality of pores may be disconnected, such that there is limited communication between the pores, separated by a solid node of material. In some embodiments, the plurality of pores have a different pore diameter. In some embodiments, the plurality of pores having a different pore area are defined by an average pore diameter for the material. The average pore diameter is calculated by adding the pore diameter of the plurality of pores and dividing by the total number of pores. In some embodiments, the average pore diameter is about 1 micron. In some embodiments, the average pore diameter is about 0.5 micron. In some embodiments, the average pore diameter is about 0.25 micron. In some embodiments, the average pore diameter is about 0.1 micron. In some embodiments, the average pore diameter is less than 1 micron. In some embodiments, the average pore diameter is less than 0.5 micron. In some embodiments, the average pore diameter is less than 0.25 micron. In some embodiments, the average pore diameter is less than 0.1 micron. In some embodiments, the average pore diameter is up to 1 micron. In some embodiments, the average pore diameter is up to 0.5 micron. In some embodiments, the average pore diameter is up to 0.25 micron. In some embodiments, the average pore diameter is up to 0.1 micron. In some embodiments, the average pore diameter is in a range of about 0.05 micron to about 1 micron. In some embodiments, the average pore diameter is in a range of about 0.1 micron to about 1 micron. In some embodiments, the average pore diameter is in a range of about 0.25 micron to about 1 micron. In some embodiments, the average pore diameter is in a range of about 0.5 micron to about 1 micron. In some embodiments, the average pore diameter is in a range of about 0.05 micron to about 0.5 micron. In some embodiments, the average pore diameter is in a range of about 0.05 micron to about 0.25 micron. In some embodiments, the average pore diameter is in a range of about 0.05 micron to about 0.1 micron.

In some embodiments, leaflets are constructed from a material having a thickness. In some embodiments, the thickness is about 0.3 mm. In some embodiments, the thickness is about 0.1 mm. In some embodiments, the thickness is about 0.075 mm. In some embodiments, the thickness is about 0.05 mm. In some embodiments, the thickness is about 0.045 mm. In some embodiments, the thickness is about 0.04 mm. In some embodiments, the thickness is about 0.035 mm. In some embodiments, the thickness is about 0.03 mm. In some embodiments, the thickness is about 0.025 mm. In some embodiments, the thickness is about 0.02 mm. In some embodiments, the thickness is about 0.015 mm. In some embodiments, the thickness is about 0.01 mm. In some embodiments, the thickness is less than 0.3 mm. In some embodiments, the thickness is less than 0.1 mm. In some embodiments, the thickness is less than 0.075 mm. In some embodiments, the thickness is less than 0.05 mm. In some embodiments, the thickness is less than 0.045 mm. In some embodiments, the thickness is less than 0.04 mm. In some embodiments, the thickness is less than 0.035 mm. In some embodiments, the thickness is less than 0.03 mm. In some embodiments, the thickness is less than 0.025 mm. In some embodiments, the thickness is less than 0.02 mm. In some embodiments, the thickness is less than 0.015 mm. In some embodiments, the thickness is less than 0.01 mm. In some embodiments, the thickness is up to 0.3 mm. In some embodiments, the thickness is up to 0.1 mm. In some embodiments, the thickness up to 0.075 mm. In some embodiments, the thickness is up to 0.05 mm. In some embodiments, the thickness is up to 0.045 mm. In some embodiments, the thickness is up to 0.04 mm. In some embodiments, the thickness is up to 0.035 mm. In some embodiments, the thickness is up to 0.03 mm. In some embodiments, the thickness is up to 0.025 mm. In some embodiments, the thickness is up to 0.02 mm. In some embodiments, the thickness is up to 0.015 mm. In some embodiments, the thickness is up to 0.01 mm. In some embodiments, the thickness is in a range of about 0.01 mm to about 0.3 mm. In some embodiments, the thickness is in a range of about 0.015 mm to about 0.3 mm. In some embodiments, the thickness is in a range of about 0.02 mm to about 0.3 mm. In some embodiments, the thickness is in a range of about 0.025 mm to about 0.3 mm. In some embodiments, the thickness is in a range of about 0.03 mm to about 0.3 mm. In some embodiments, the thickness is in a range of about 0.035 mm to about 0.3 mm. In some embodiments, the thickness is in a range of about 0.04 mm to about 0.3 mm. In some embodiments, the thickness is in a range of about 0.01 mm to about 0.1 mm. In some embodiments, the thickness is in a range of about 0.01 mm to about 0.075 mm. In some embodiments, the thickness is in a range of about 0.01 mm to about 0.05 mm. In some embodiments, the thickness is in a range of about 0.015 mm to about 0.075 mm. In some embodiments, the thickness is in a range of about 0.02 mm to about 0.075 mm. In some embodiments, the thickness is in a range of about 0.025 mm to about 0.075 mm. In some embodiments, the thickness is in a range of about 0.03 mm to about 0.075 mm. In some embodiments, the thickness is in a range of about 0.035 mm to about 0.075 mm. In some embodiments, the thickness is in a range of about 0.04 mm to about 0.075 mm. In some embodiments, the thickness is in a range of about 0.045 mm to about 0.075 mm. In some embodiments, the thickness is in a range of about 0.01 mm to about 0.05 mm. In some embodiments, the thickness is in a range of about 0.015 mm to about 0.05 mm. In some embodiments, the thickness is in a range of about 0.02 mm to about 0.05 mm. In some embodiments, the thickness is in a range of about 0.025 mm to about 0.05 mm. In some embodiments, the thickness is in a range of about 0.03 mm to about 0.05 mm. In some embodiments, the thickness is in a range of about 0.035 mm to about 0.05 mm. In some embodiments, the thickness is in a range of about 0.04 mm to about 0.05 mm. In some embodiments, the thickness is in a range of about 0.045 mm to about 0.05 mm.

In some embodiments, leaflets are constructed from multiple layers of a material, wherein the multiple layers of the material have a total thickness. In some embodiments, the total thickness is about 0.3 mm. In some embodiments, the total thickness is about 0.1 mm. In some embodiments, the total thickness is about 0.075 mm. In some embodiments, the total thickness is about 0.05 mm. In some embodiments, the total thickness is about 0.045 mm. In some embodiments, the total thickness is about 0.04 mm. In some embodiments, the total thickness is about 0.035 mm. In some embodiments, the total thickness is about 0.03 mm. In some embodiments, the total thickness is about 0.025 mm. In some embodiments, the total thickness is about 0.02 mm. In some embodiments, the total thickness is about 0.015 mm. In some embodiments, the total thickness is about 0.01 mm. In some embodiments, the total thickness is less than 0.3 mm. In some embodiments, the total thickness is less than 0.1 mm. In some embodiments, the total thickness is less than 0.075 mm. In some embodiments, the total thickness is less than 0.05 mm. In some embodiments, the total thickness is less than 0.045 mm. In some embodiments, the total thickness is less than 0.04 mm. In some embodiments, the total thickness is less than 0.035 mm. In some embodiments, the total thickness is less than 0.03 mm. In some embodiments, the total thickness is less than 0.025 mm. In some embodiments, the total thickness is less than 0.02 mm. In some embodiments, the total thickness is less than 0.015 mm. In some embodiments, the total thickness is less than 0.01 mm. In some embodiments, the total thickness is up to 0.3 mm. In some embodiments, the total thickness is up to 0.1 mm. In some embodiments, the total thickness up to 0.075 mm. In some embodiments, the total thickness is up to 0.05 mm. In some embodiments, the total thickness is up to 0.045 mm. In some embodiments, the total thickness is up to 0.04 mm. In some embodiments, the total thickness is up to 0.035 mm. In some embodiments, the total thickness is up to 0.03 mm. In some embodiments, the total thickness is up to 0.025 mm. In some embodiments, the total thickness is up to 0.02 mm. In some embodiments, the total thickness is up to 0.015 mm. In some embodiments, the total thickness is up to 0.01 mm. In some embodiments, the total thickness is in a range of about 0.01 mm to about 0.3 mm. In some embodiments, the total thickness is in a range of about 0.015 mm to about 0.3 mm. In some embodiments, the total thickness is in a range of about 0.02 mm to about 0.3 mm. In some embodiments, the total thickness is in a range of about 0.025 mm to about 0.3 mm. In some embodiments, the total thickness is in a range of about 0.03 mm to about 0.3 mm. In some embodiments, the total thickness is in a range of about 0.035 mm to about 0.3 mm. In some embodiments, the total thickness is in a range of about 0.04 mm to about 0.3 mm. In some embodiments, the total thickness is in a range of about 0.01 mm to about 0.1 mm. In some embodiments, the total thickness is in a range of about 0.01 mm to about 0.075 mm. In some embodiments, the total thickness is in a range of about 0.01 mm to about 0.05 mm. In some embodiments, the total thickness is in a range of about 0.015 mm to about 0.075 mm. In some embodiments, the total thickness is in a range of about 0.02 mm to about 0.075 mm. In some embodiments, the total thickness is in a range of about 0.025 mm to about 0.075 mm. In some embodiments, the total thickness is in a range of about 0.03 mm to about 0.075 mm. In some embodiments, the total thickness is in a range of about 0.035 mm to about 0.075 mm. In some embodiments, the total thickness is in a range of about 0.04 mm to about 0.075 mm. In some embodiments, the total thickness is in a range of about 0.045 mm to about 0.075 mm. In some embodiments, the total thickness is in a range of about 0.01 mm to about 0.05 mm. In some embodiments, the total thickness is in a range of about 0.015 mm to about 0.05 mm. In some embodiments, the total thickness is in a range of about 0.02 mm to about 0.05 mm. In some embodiments, the total thickness is in a range of about 0.025 mm to about 0.05 mm. In some embodiments, the total thickness is in a range of about 0.03 mm to about 0.05 mm. In some embodiments, the total thickness is in a range of about 0.035 mm to about 0.05 mm. In some embodiments, the total thickness is in a range of about 0.04 mm to about 0.05 mm. In some embodiments, the total thickness is in a range of about 0.045 mm to about 0.05 mm.

In some embodiments, leaflets are constructed from multiple layers of material, wherein the multiple layers of material have a total thickness. In some embodiments, leaflets are constructed from multiple layers of material, where the layers are substantially similar in thickness. In other embodiments, leaflets are constructed from multiple layers of material were the layers differ significantly in thickness. For example, a leaflet may be constructed from two layers, one of which is approximately 0.040 mm thick, and another is approximately 0.005 mm thick, resulting in a total thickness of 0.045 mm.

Figure 13:
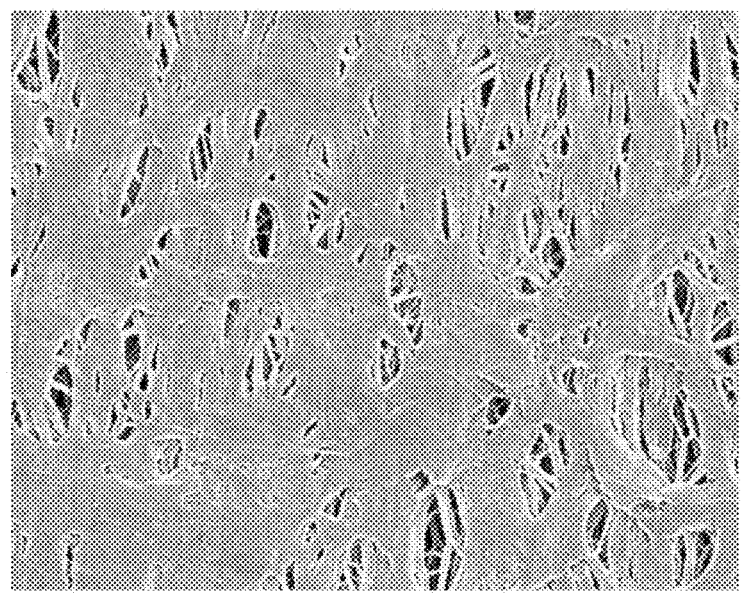
FIG. 13 is a SEM image of a leaflet illustrating a material having an average pore area, an average pore diameter, and a surface porosity, according to an embodiment.

As illustrated in FIG. 13, in some embodiments leaflets are constructed from a material having a surface porosity. In some embodiments, the surface porosity may range up to 15%, but not be less than 1%. In some embodiments, the surface porosity is about 15%. In some embodiments, the surface porosity is about 14%. In some embodiments, the surface porosity is about 13%. In some embodiments, the surface porosity is about 12%. In some embodiments, the surface porosity is about 11%. In some embodiments, the surface porosity is about 10%. In some embodiments, the surface porosity is about 9%. In some embodiments, the surface porosity is about 8%. In some embodiments, the surface porosity is about 7%. In some embodiments, the surface porosity is about 6%. In some embodiments, the surface porosity is about 5%. In some embodiments, the surface porosity is about 4%. In some embodiments, the surface porosity is about 3%. In some embodiments, the surface porosity is about 2%. In some embodiments, the surface porosity is about 1%. In some embodiments, the surface porosity is less than 15%. In some embodiments, the surface porosity is less than 14%. In some embodiments, the surface porosity is less than 13%. In some embodiments, the surface porosity is less than 12%. In some embodiments, the surface porosity is less than 11%. In some embodiments, the surface porosity is less than 10%. In some embodiments, the surface porosity is less than 9%. In some embodiments, the surface porosity is less than 8%. In some embodiments, the surface porosity is less than 7%. In some embodiments, the surface porosity is less than 6%. In some embodiments, the surface porosity is less than 5%. In some embodiments, the surface porosity is less than 4%. In some embodiments, the surface porosity is less than 3%. In some embodiments, the surface porosity is less than 2%. In some embodiments, the surface porosity is in a range of about 1% to about 15%. In some embodiments, the surface porosity is in a range of about 2% to about 15%. In some embodiments, the surface porosity is in a range of about 3% to about 15%. In some embodiments, the surface porosity is in a range of about 4% to about 15%. In some embodiments, the surface porosity is in a range of about 5% to about 15%. In some embodiments, the surface porosity is in a range of about 6% to about 15%. In some embodiments, the surface porosity is in a range of about 7% to about 15%. In some embodiments, the surface porosity is in a range of about 8% to about 15%. In some embodiments, the surface porosity is in a range of about 1% to about 14%. In some embodiments, the surface porosity is in a range of about 1% to about 13%. In some embodiments, the surface porosity is in a range of about 1% to about 12%. In some embodiments, the surface porosity is in a range of about 1% to about 11%. In some embodiments, the surface porosity is in a range of about 1% to about 10%. In some embodiments, the surface porosity is in a range of about 1% to about 9%. In some embodiments, the surface porosity is in a range of about 1% to about 8%. In some embodiments, the surface porosity is in a range of about 1% to about 7%. In some embodiments, the surface porosity is in a range of about 1% to about 6%. In some embodiments, the surface porosity is in a range of about 1% to about 5%. In some embodiments, the surface porosity is in a range of about 1% to about 4%. In some embodiments, the surface porosity is in a range of about 1% to about 3%. In some embodiments, the surface porosity is in a range of about 1% to about 2%. In some embodiments, the surface porosity is in a range of about 1% to about 8%. In some embodiments, the surface porosity is in a range of about 2% to about 8%. In some embodiments, the surface porosity is in a range of about 3% to about 8%. In some embodiments, the surface porosity is in a range of about 4% to about 8%. In some embodiments, the surface porosity is in a range of about 1% to about 7%. In some embodiments, the surface porosity is in a range of about 1% to about 6%. In some embodiments, the surface porosity is in a range of about 1% to about 5%. In some embodiments, the surface porosity is in a range of about 1% to about 4%. In some embodiments, the surface porosity is in a range of about 1% to about 3%. In some embodiments, the surface porosity is in a range of about 1% to about 2%. In some embodiments, the surface porosity is in a range of about 2% to about 6%. In some embodiments, the surface porosity is in a range of about 3% to about 5%. In some embodiments, the surface porosity is in a range of about 1% to less than 15%.

In some embodiments, leaflets are constructed from multiple layers of material, at least two layers of which are anisotropic with differing orientations. For example, in some embodiments, two layers may be anisotropic with orientations that are perpendicular to one another. In other embodiments, two layers may be anisotropic with orientations that are offset by less than 90 degrees, but greater than 10 degrees, relative to each other. In some embodiments, two layers may be anisotropic with orientations that are not parallel relative to each other. In some embodiments, two layers may be anisotropic with orientations that are offset by about 90 degrees to about 10 degrees, about 85 degrees to about 10 degrees, about 80 degrees to about 10 degrees, about 75 degrees to about 10 degrees, about 70 degrees to about 10 degrees, about 65 degrees to about 10 degrees, about 60 degrees to about 10 degrees, about 55 degrees to about 10 degrees, about 50 degrees to about 10 degrees, about 45 degrees to about 10 degrees, about 40 degrees to about 10 degrees, about 35 degrees to about 10 degrees, about 30 degrees to about 10 degrees, about 25 degrees to about 10 degrees, about 20 degrees to about 10 degrees, about 15 degrees to about 10 degrees relative to each other. In some embodiments, two layers may be anisotropic with orientations that are offset by about 90 degrees to about 15 degrees, about 90 degrees to about 20 degrees, about 90 degrees to about 25 degrees, about 90 degrees to about 30 degrees, about 90 degrees to about 35 degrees, about 90 degrees to about 40 degrees, about 90 degrees to about 45 degrees, about 90 degrees to about 50 degrees, about 90 degrees to about 55 degrees, about 90 degrees to about 60 degrees, about 90 degrees to about 65 degrees, about 90 degrees to about 70 degrees, about 90 degrees to about 75 degrees, about 90 degrees to about 80 degrees, about 90 degrees to about 85 degrees relative to each other. In some embodiments, two layers may be anisotropic with orientations that are offset by about 90 degrees relative to each other. In some embodiments, two layers may be anisotropic with orientations that are offset by about 85 degrees relative to each other. In some embodiments, two layers may be anisotropic with orientations that are offset by about 80 degrees relative to each other. In some embodiments, two layers may be anisotropic with orientations that are offset by about 75 degrees relative to each other. In some embodiments, two layers may be anisotropic with orientations that are offset by about 70 degrees relative to each other. In some embodiments, two layers may be anisotropic with orientations that are offset by about 65 degrees relative to each other. In some embodiments, two layers may be anisotropic with orientations that are offset by about 60 degrees relative to each other. In some embodiments, two layers may be anisotropic with orientations that are offset by about 55 degrees relative to each other. In some embodiments, two layers may be anisotropic with orientations that are offset by about 50 degrees relative to each other. In some embodiments, two layers may be anisotropic with orientations that are offset by about 45 degrees relative to each other. In some embodiments, two layers may be anisotropic with orientations that are offset by about 40 degrees relative to each other. In some embodiments, two layers may be anisotropic with orientations that are offset by about 35 degrees relative to each other. In some embodiments, two layers may be anisotropic with orientations that are offset by about 30 degrees relative to each other. In some embodiments, two layers may be anisotropic with orientations that are offset by about 25 degrees relative to each other. In some embodiments, two layers may be anisotropic with orientations that are offset by about 20 degrees relative to each other. In some embodiments, two layers may be anisotropic with orientations that are offset by about 15 degrees relative to each other. In some embodiments, two layers may be anisotropic with orientations that are offset by about 10 degrees relative to each other.

Figure 9A:
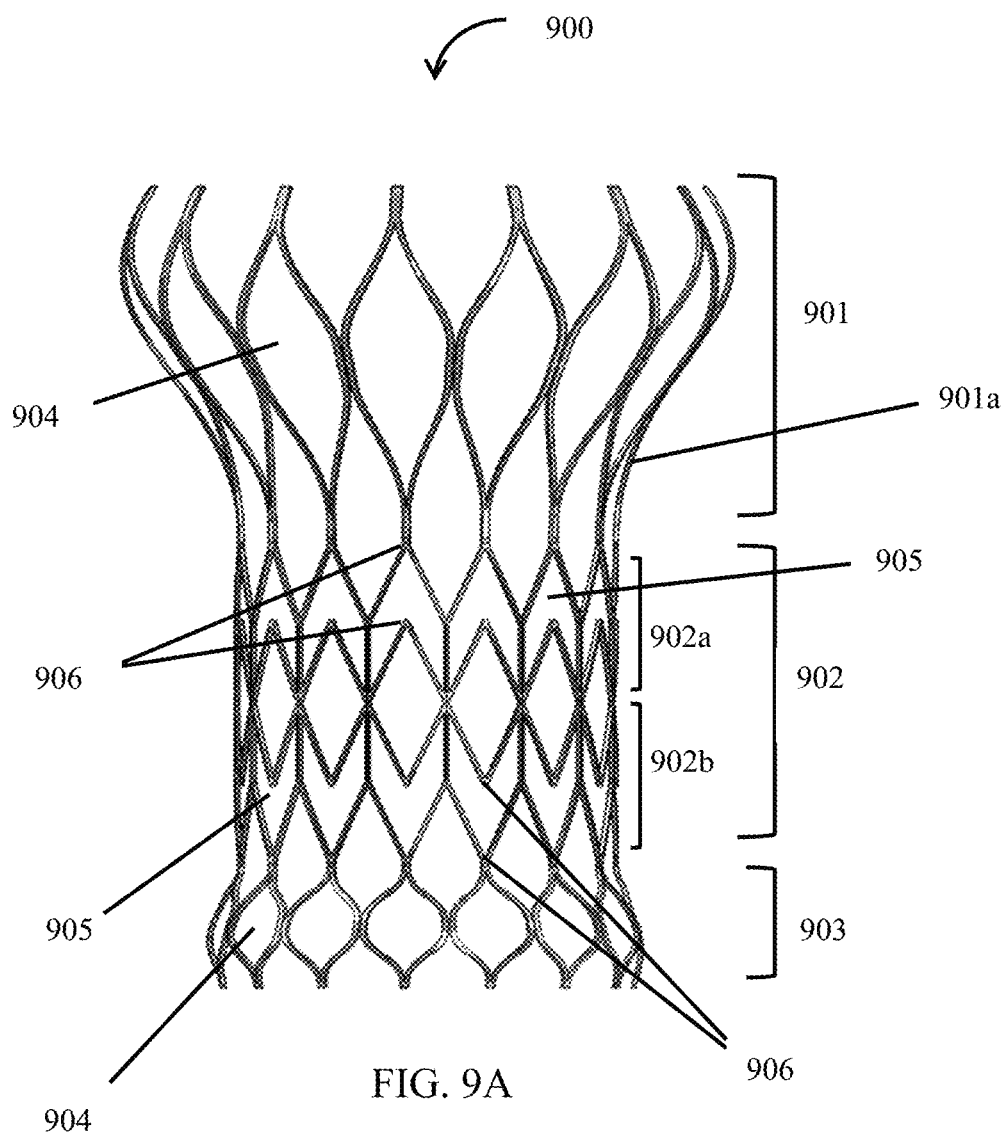
FIG. 9A depicts a stent according to an embodiment.

Disclosed herein are transcatheter stents with valved conduits. An exemplary stent is shown in FIG. 9A. The stent 900 has three contiguous portions or regions, a proximal portion 901, an intermediate portion 902, and a distal portion 903. The proximal portion 901 has a relatively larger cross-section in the expanded configuration, while the intermediate portion 902 and the distal portion 903 have relatively smaller cross-section in the expanded configuration. The intermediate portion 902 is in the form of a cylinder having a substantially constant diameter along its length. In some embodiments, the intermediate portion 902 may have a variable diameter along its length. A transition section 901a may taper inwardly from the proximal portion 901 to the intermediate portion 902. Further, the proximal portion 901 faces the aorta and the distal portion 903 faces the annulus when the stent is deployed.

In some embodiments, proximal portion 901 and the distal portion 903 is made of a series of cells arranged in one or more annular rows around the stent. The cells may be spindle-shaped structures 904 as shown in FIG. 9A, and may be defined as structures having a wider central section with tapering ends. For example, in FIG. 9A the proximal portion 901 and the distal portion 903 are each made up of two annular rows of spindle shaped structures. In other embodiments, proximal portion 901 and the distal portion 903 may each have three, or four, or five annular rows of spindle shaped structures. It should be appreciated that as the number of annular rows increase, the area formed by each spindle shaped structure may decrease correspondingly, to maintain the length of the proximal portion 901 and the distal portion 903. Further, the area of spindle shaped structures in the proximal portion 901 may be larger than the area of spindle shaped structures in the distal portion 903. It will be appreciated that the shape of the cells are not limited to spindle shaped structures, and can also encompass other shapes such as diamond shapes, rhomboid shapes, and the like.

Figure 9B:
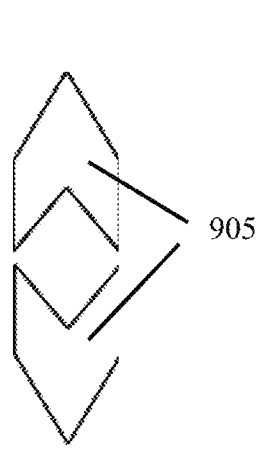
FIG. 9B depicts a pair of opposing chevron shaped structures according to an embodiment.

In some embodiments, the intermediate portion 902 is made of a series of chevron shaped structures 905 arranged in two or more annular rows opposing to each other. For clarity, an isolated pair of opposing chevron shaped structures are depicted in FIG. 9B. For example, in FIG. 9A, the intermediate portion 902 has two annular rows 902a, 902b of chevron shaped structures 905 opposing each other. Row 902a is towards the proximal portion 901, and row 902b is towards the distal portion 903. The number of chevron shaped structures 905 in each annular row may vary. For example, in FIG. 9A there are 12 chevron shaped structures 905 in each annular row 902a, 902b. In other embodiments, the number of chevron shaped structures 905 in each annular row may vary from 4 to 24.

Figure 9C:
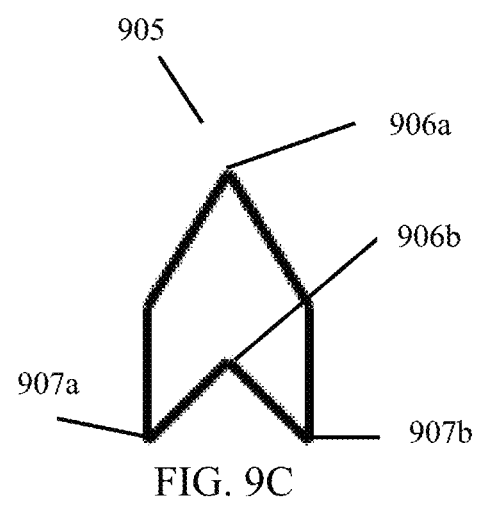
FIG. 9C depicts a single chevron structure with median and lateral vertices.

In some embodiments, the intermediate portion 902 of the stent 900 further has one or more attachment points 906 to facilitate attachment of the conduit and/or the valve structure, as shown in FIG. 9A. The attachment points 906 are present on the median vertices of one or more chevron shaped structures 905. For example, FIG. 9C shows a single chevron shaped structure 905 with a pair of median vertices 906a, 906b, and a pair of lateral vertices 907a, 907b. Proximal median vertex 906a faces towards the proximal portion 901 of the stent, and distal median vertex 906b faces towards the distal portion 903 of the stent. Preferably, the conduit and/or the valve structure may be attached to the proximal and distal median vertices (906a, 906b) of the chevron shaped structures 905 present in the intermediate portion 902 of the stent. The number of attachment points may vary, ranging from 6 to 20, depending on the size of the stent and the conduit/valve structure. The conduit and/or valve structure may be attached to the attachment points 906 by suturing, welding, fusion, applying an adhesive, and combinations thereof. The attachment points 906 are disposed at a selected distance between each other such that the distance between the attachment points do not substantially change when the stent is collapsed (crimped) from an expanded configuration.

Figures 9D, 9E:
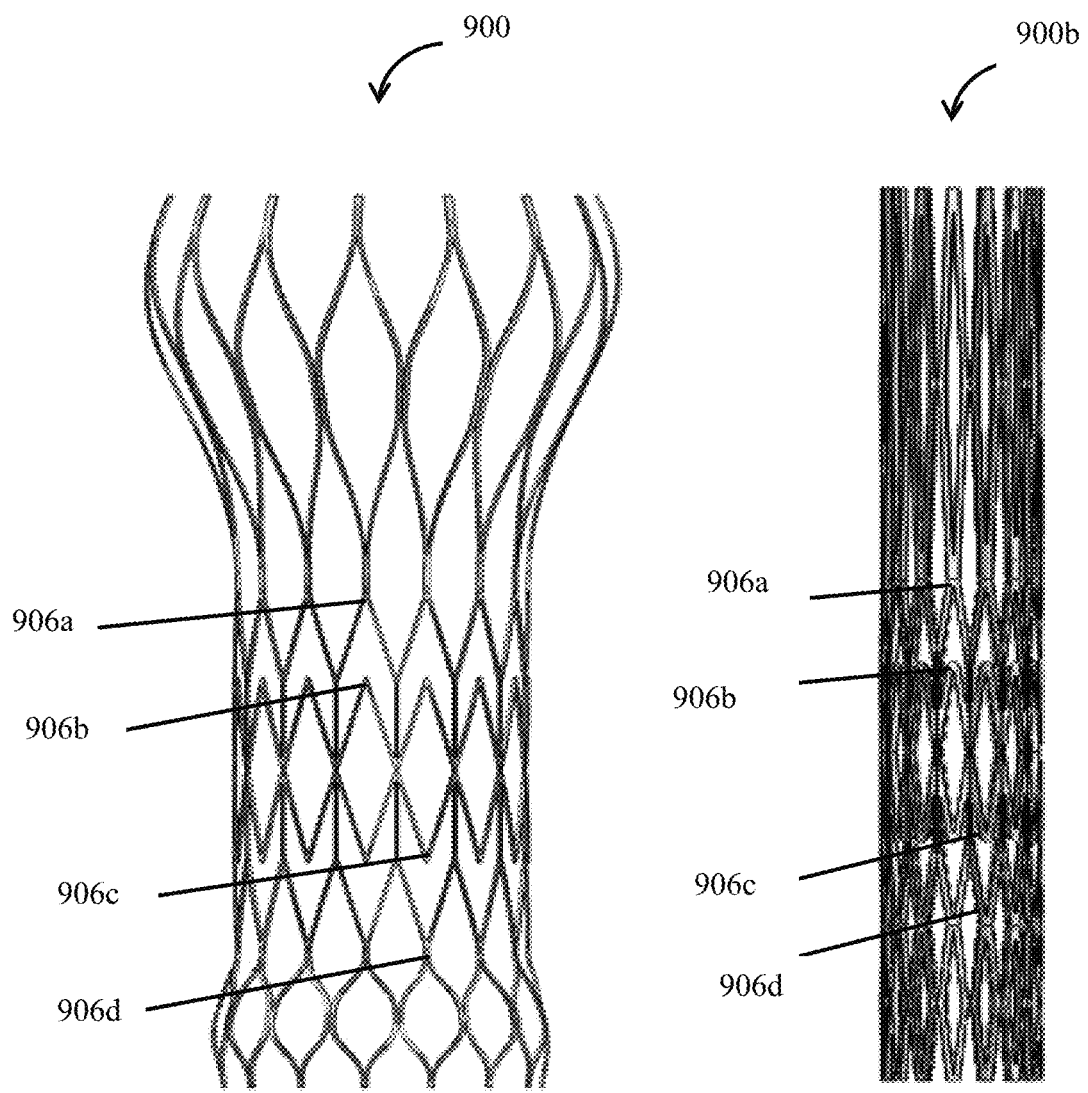
FIG. 9D depicts the stent with a plurality of attachment points in expanded configuration.
FIG. 9E depicts the stent with a plurality of attachment points in collapsed configuration.

In FIG. 9D and FIG. 9E, the stent 900 in FIG. 9D is shown in expanded configuration with a plurality of attachment points 906a, 906b, 906c, and 906d in the intermediate portion 902. When the stent 900b is collapsed (FIG. 9E), the distance between the attachment points 906a and 906b, between attachment points 906c and 906d, and between attachment points 906b and 906c essentially remain the same. Attachment points 906c and 906d rotate with respect to 906a and 906b and compensates for the longitudinal stretching of the stent. In addition, 906a and 906b translate together and 906c and 906d translate together in opposite directions. Therefore, although the intermediate portion 902 changes length when it undergoes the transition from expanded configuration to the collapsed configuration, the length of multiple regions (in this example 906a-906b, 906b-906c, and 906c-906d) remain substantially the same.

Due to the non-stretching nature of the portions of the stent, it can accommodate conduits and valve structures made of non-stretch material. Non-limiting examples of non-stretch material that can be used to make the conduits and valve structures are polytetrafluoroethylene (PTFE), expanded polytetrafluoroethylene (ePTFE), polyethylene terephthalate (PET), polydimethyl siloxane (PDMS), polyethylene (PE), polypropylene (PP), polyesters, polycarbonates, polyvinyl chloride (PVC), hydrogels, a methacrylate polymer, a vinyl benzene polymer, a 2-hydroxyethyl acrylate polymer, a butyl acrylate polymer, a 2-ethylhexyl acrylate polymer, a vinyltrimethoxysilane polymer, a vinyltriethoxysilane polymer, a vinyltoluene polymer, an α-methyl styrene polymer, a chlorostyrene polymer, a styrenesulfonic acid polymer, and a combination thereof.

The stent disclosed herein may be made from cobalt, titanium, nickel, chromium, stainless steel, a polymer, a pseudo-elastic metal, and alloys thereof, and any combination thereof. In some embodiments, the stent may be made from nickel titanium alloy nitinol. In some embodiments, the stents disclosed herein are self-expandable stents. Self-expandable stent as used herein means that a structure/component has a mechanical memory to return to the expanded or deployed configuration. Mechanical memory may be imparted to the framework structure that forms stent by thermal treatment to achieve a spring temper in stainless steel, for example, or to set a shape memory in a susceptible metal alloy, such as nitinol, or a polymer.

It will be understood by one of ordinary skill in the art that the length of each portion of the stent 900 may vary according to application and is not limited to the proportions shown in FIG. 9A. For example, in one embodiment the length of the intermediate portion 902 is equal to the length of the leaflet of a valve structure described herein, for example length B of leaflet 701 as shown in FIG. 7D. In some embodiments, the length of the intermediate portion 902 is such that the distance between the two attachment points 906a and 906c is equal to the length B of the leaflet 701 shown in FIG. 7D. In some embodiments, the length of the intermediate portion 902 may be about 5 mm to about 40 mm, about 5 mm to about 30 mm, about 8 mm to about 25 mm, about 10 mm to about 20 mm, and ranges between them. In some embodiments, the length of the proximal portion 901 may be from about 5 mm to about 50 mm, about 5 mm to about 40 mm, about 5 mm to about 30 mm, about 5 mm to about 20 mm, about 25 mm to about 50 mm, or about 35 mm to about 50 mm. In some embodiments, the distal portion 903 may have a length of about 3 mm to about 20 mm, about 3 mm to about 15 mm, about 3 mm to about 10 mm, or about 3 mm to about 5 mm or a value within any of these ranges. It should be appreciated that the length described herein of various portions may not vary irrespective of whether the stent is in expanded configuration (deployed state) or collapsed configuration (crimped state).

In some embodiments, the diameter of the proximal portion 901 may be from about 5 mm to about 50 mm, about 5 mm to about 40 mm, about 5 mm to about 30 mm, about 5 mm to about 20 mm, about 5 mm to about 10 mm, or any individual width or range encompassed by these example widths. In some embodiments, the proximal portion 901 of the stent may have substantially constant diameter along its length. In some embodiments, the proximal portion 901 may taper inwardly towards the intermediate portion 902.

In some embodiments, the diameter of the intermediate portion 902 may be from about 5 mm to about 50 mm, about 5 mm to about 40 mm, about 5 mm to about 30 mm, about 5 mm to about 20 mm, about 5 mm to about 10 mm, or any individual width or range encompassed by these example widths. In some embodiments, the intermediate portion 902 of the stent may have substantially constant diameter along its length. In some embodiments, the intermediate portion 902 may have variable diameter along its length.

In some embodiments, the diameter of the distal portion 903 may be from about 5 mm to about 50 mm, about 5 mm to about 40 mm, about 5 mm to about 30 mm, about 5 mm to about 20 mm, about 5 mm to about 10 mm, or any individual width or range encompassed by these example widths. In some embodiments, the distal portion 903 of the stent may have substantially constant diameter along its length. In some embodiments, the free edge of the distal portion 903 may taper outward.

FIG. 10 illustrates an embodiment of a valve structure 1000 that may be attached to the stent 900. The valve 1000 is made of a single piece of biocompatible material, having 3 leaflets 1001. A commissure 1002 exists between each leaflet. The outer sinus edge and inner sinus edge of each leaflet can be attached to the intermediate portion 902 of the stent. In some embodiments, each leaflet of the valve is attached to the intermediate portion 902 at a pair of attachment points, and each attachment point present on opposing annular row of chevron shaped structures. For example, the regions 1000a-c on the valve may be attached to the attachment points 906a-c present on the intermediate portion of the stent, as shown in FIG. 9D. For example, 1000a is attached to 906a, 1000b is attached to 906b, and 1000c is attached to 906c. Because the distance between the attachment points 906a-906b and 906b-906c do not change when the stent is expanded or collapsed, a valve made from a non-stretchable material may be used. In addition, other regions of the leaflet can also be used to attach the valve to the stent, such as the commissure region 1002. In some embodiments, the valve is directly attached to the stent. In other embodiments, the valve is attached to the inner surface of a conduit, and the conduit is attached to the stent. In further embodiments, the valve and the conduit are concurrently attached to the same regions of the stent.

Figure 11A:
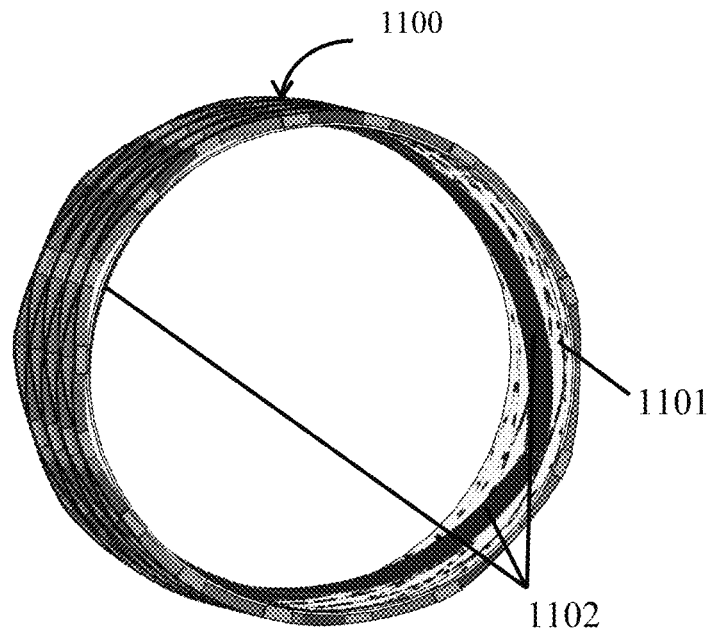
FIG. 11A shows a stent with a valve in an open position.
Figure 11B:
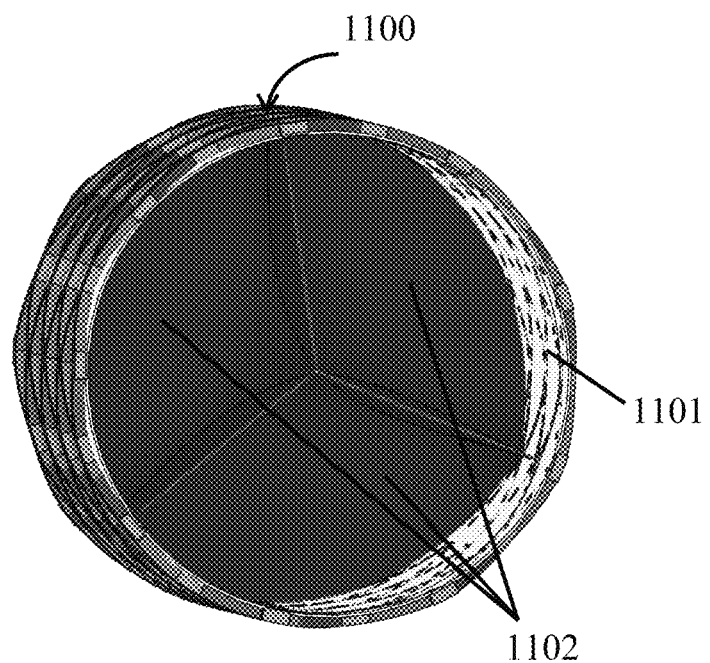
FIG. 11B shows a stent with a valve in a closed position.
Figure 12A:
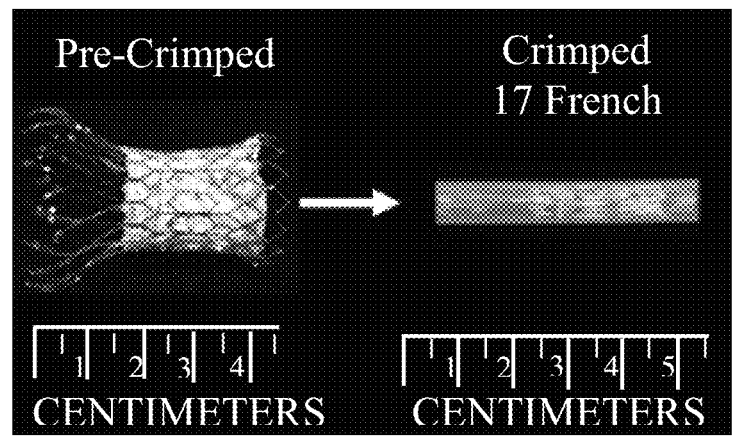
FIG. 12A shows a stent with a valved conduit in deployed configuration and crimped configuration, where the conduit and the valve are non-stretchable.
Figure 12B:
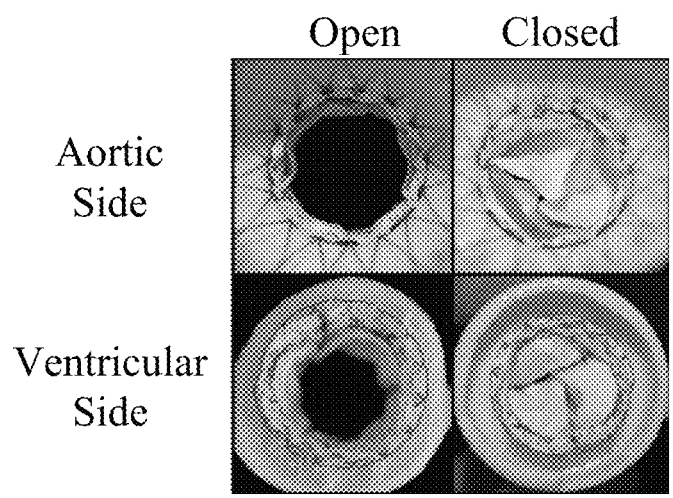
FIG. 12B shows a stent with a valve in an open configuration and a closed configuration.

In some embodiments, the stent includes a valved conduit (a conduit having valve). In other embodiments, the stent includes a valve directly attached to the stent. FIG. 11A and FIG. 11B shows an exemplary embodiment of stent 1100 having a conduit 1101 disposed on an inner surface of the stent 1100, and a valve 1102. In some embodiments, the valve 1102 may be attached directly to the inner surface of the stent 1100, without conduit 1101 disposed between the valve and the stent. In another embodiment, a sheath may also be located on the outer surface of the stent. The conduit and/or the sheath may cover all or only a portion of the length and circumference of the stent. Further, the valve contained within the stents of such embodiments can have any number of leaflets. For example, the stent 1100 in FIG. 11B has three leaflets; however, embodiments include stents with valves having two leaflets as illustrated in FIG. 2B and FIG. 3B or one leaflet as illustrated in FIG. 1A. Similarly, the valved conduits described above and exemplified in FIG. 1A, FIG. 1B, FIG. 2A, FIG. 2B, FIG. 3A, FIG. 3B can include three leaflets. Each leaflet of the stent 1100 of various embodiments may include a gap when the valve is in open position (FIG. 11A) and therefore, may have a width that is shorter than the portion of the conduit between attachment points.

Figure 8A:
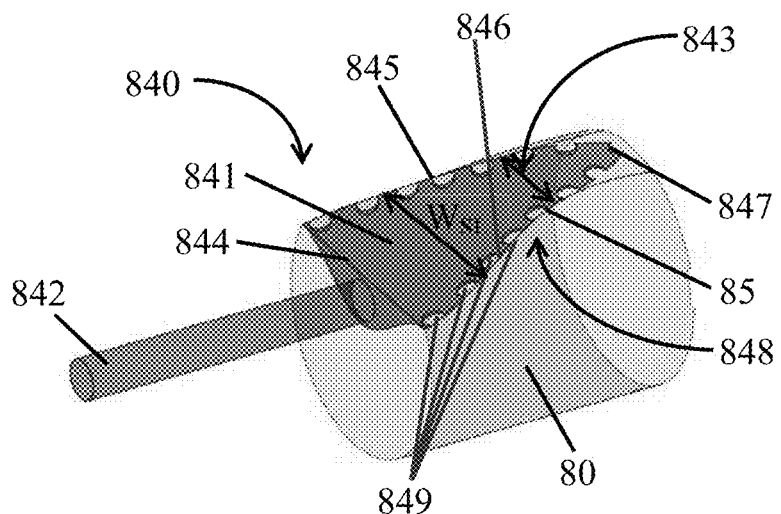
FIG. 8A shows a perspective view of a fixing stencil.
Figure 8B:
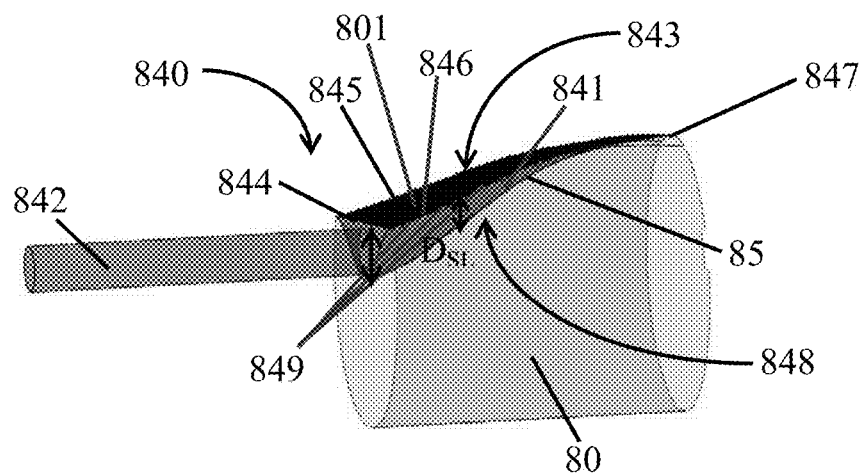
FIG. 8B shows another perspective view of a fixing stencil.

Various embodiments are directed to a fixing stencil 840. In some embodiments as illustrated in FIG. 8A and FIG. 8B, the fixing stencil 840 may include a stencil head 841 and handle 842. The stencil head 841 may substantially triangular flat surface 843 having a base 844, a first outer edge 845, a second outer edge 846, and a tip 847, and a triangular curved surface 848. In various embodiments, the triangular curved surface 848 may be tapered laterally from a longitudinal axis extending from the handle 842 to first outer edge 845 and from the longitudinal axis to the second outer edge 847. The triangular curved surface 848 may be further curved from the base 844 to the tip 847 creating a complex of curved surfaces having a tetrahedral shape extending away from the base 844 to the tip 847. In some embodiments, the stencil head 841 may further include holes or slots 849 along the first outer edge 845 and second outer edge 846 to allow physical fixturing, for example, suturing, welding, adhesive application, or other means for attaching the leaflet 801 to the conduit 80 without contacting the stencil head 841. In other embodiments, the stencil head 841 may be pierceable or locally destructible along the first outer edge 845 and second outer edge 846 to allow removal of the stencil head 841 after fixturing.

The handle 842 of various embodiments may be any means for manipulating and holding the fixing stencil 840 in place while the valve is attached to the conduit. For example, in some embodiments, the handle may be sized and shaped to be gripped by a human hand. In other embodiments, the handle may be include one or more tabs or wings sized and shaped for holding the fixing stencil to the conduit and valve using surgical tools, claps, vice grips, or other tools.

The size of the stencil head 841 may vary depending on the size and shape of the valve to 8 that will be produced using the fixing stencil 840. In general, the length, $B_s$, from the base 844, extending from the handle, to the tip 845, of the stencil head 841 may be substantially the same length, B, as the leaflet 801. The variable width, $W_{SL}$, of the substantially triangular flat surface may substantially correspond to the variable width of the triangular leaflet and the variable depth, $D_{SL}$, of the triangular curved surface 884 may substantially corresponding to the depth of the sinus 830. Thus, the stencil head may be configured to have substantially the same shape and volume as the sinus 830 created between the leaflet 801 and the portion of the conduit 80 making up the tapered dimple 85.

In various embodiments, the width, $W_{SL}$, of the stencil head 841 may be about 1 mm to about 10 mm, about 2 mm to about 7 mm, about 2 mm to about 5 mm, about 20 mm to about 40 mm, about 10 mm to about 30 mm, or any individual width or range encompassed by these example widths. The length, $B_S$, of the stencil head 841 may be about 5 mm to about 40 mm, about 5 mm to about 30 mm, about 8 mm to about 25 mm, about 10 mm to about 20 mm, or any individual length or range encompassed by these example lengths. The length of the first outer edge 845 and second outer edge 846 may each, individually, be about 5 mm to about 45 mm, about 5 mm to about 35 mm, about 8 mm to about 30 mm, about 10 mm to about 20 mm, or any individual length or range encompassed by these example lengths. The depth, $D_{SL}$, of the stencil head 841 at the base 844 may be about 1 mm to about 10 mm, about 1 mm to about 7 mm, about 1 mm to about 5 mm, or any individual depth or range encompassed by these example depths.

In some embodiments, the fixing stencil 840 may further include stabilizing components the stencil head 841 during fixturing. For example, the stabilizing components may include a clamp positioned to hold the tapered dimple 85 or an apparatus that substantially fills the remainder of the conduit. In certain embodiments, the stencil head 841 may be capable of transmitting heat to the conduit to aid in fixturing by fusing the leaflet 801 to the conduit 80 or aiding in deformation of the conduit 80 creating a sinus bulge at the sinus when the fixing stencil 840 is removed.

Further embodiments are directed to methods for making the valved conduits described above. Such embodiments may include the steps of inverting a conduit, bending a portion of the conduit to create a tapered dimple, attaching a leaflet to the conduit on a surface surrounding the tapered dimple, and reverting the conduit placing the leaflet on an inner surface of the conduit. The step of attaching can be carried out by suturing, welding, fusing, using an adhesive, and the like or combinations thereof. In some embodiments, the method may further include the step of deforming the conduit to produce a sinus bulge. In some embodiments, bending can be carried out using a fixing stencil configured to hold conduit in a bent form creating a tapered dimple. The fixing stencil may have substantially the same shape as the tapered dimple. In various embodiments, the fixing stencil may have one or more of the parts described above.

In some embodiments, a method of making a valve may include the step of cutting a valve structure from a biocompatible material. In certain embodiments, the step of cutting the valve structure may be preceded by a step of marking the biocompatible material, and in some embodiments, marking may be carried out by tracing a valve structure stencil having substantially the same shape as the valve structure onto the biocompatible material. In other embodiments, the marking can be carried out using a stamp having substantially the same shape as the valve structure. In still other embodiments, step of cutting can be carried out using a die cutting machine. Where the leaflets of the valve comprise more than one layer of the material, in some embodiments, two or more layers of the material may be attached to each other. In some embodiments, the two or more layers may be attached through one or more of the following: physical connections, such as sutures or clamps, welding, sintering, heating, such as applied heat through one or more plates, single or concentric cylinders, or laser, chemical welding, adhesive, static electric or frictional forces. For purposes of this disclosure, in embodiments where the layers of the material are attached to make the leaflet but distinction between the layers has been lost, such leaflet should still be considered to have more than one layer.

In some embodiment, the method of making a valved conduit may further include the step of marking an inner surface of the conduit with a location form attaching the leaflet to the conduit, thereby providing proper placement and alignment of the leaflets. Marking can be carried out by various means. For example, in some embodiments, marking can be carried out using a sinus stencil may be provided, and the marking on the inner surface of the conduit can be substantially the same as the sinus stencil. In such embodiments, the sinus stencil may have a shape and dimension for showing the location of the tapered dimple on the unbent inner surface of the conduit. Therefore, the sinus stencil may be wider than the valve structure, but the markings may have essentially the same shape as the leaflet after the conduit is bent.

Example 1

Figure 14E:
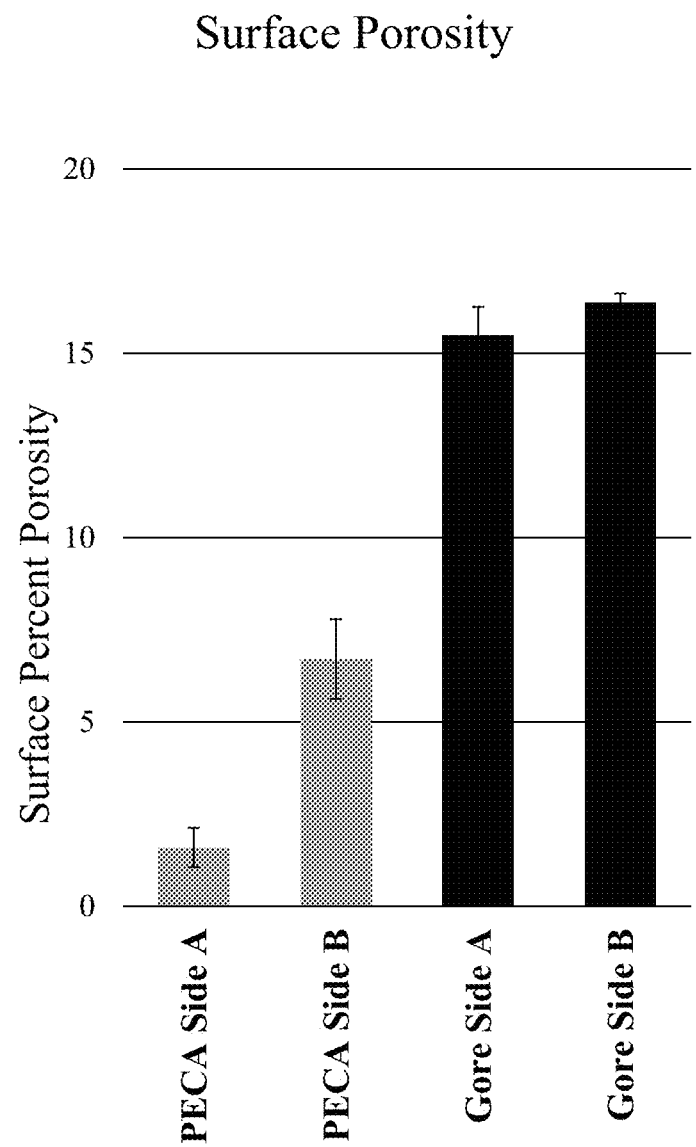
FIG. 14E depicts the quantification of the SEM images in FIGS. 14A, 14B, 14C, and 14D.

The objective of the study was to compare the microstructure and material properties of a multi-layer leaflet (termed PECA or PECA Leaflet Material) according to some embodiments described above to a multi-layer leaflet currently marketed (termed Gore or Gore Preclude Membrane having a total average thickness of 0.1 mm). According to some embodiments described above, the PECA Leaflet Material comprises a multi-layer leaflet made of ePTFE having a total thickness of 0.045 mm, wherein the multi-layers of the leaflet are anisotropic with orientations that are offset by less than 90 degrees, but greater than 10 degrees, relative to each other. The PECA Leaflet Material, depicted in FIG. 14B (side A) and FIG. 14D (side B), has a reduction in surface percent porosity when compared to Gore, depicted in FIG. 14A (side A) and FIG. 14C (side B). The quantification of these data are illustrated in FIG. 14E.

Figure 15A:
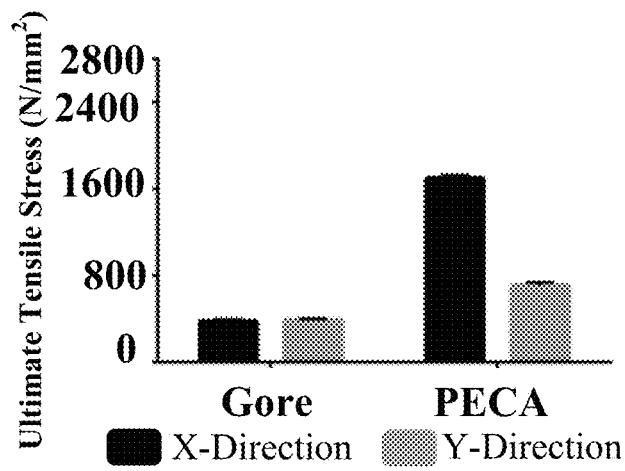
FIG. 15A illustrates a leaflet having an ultimate tensile stress according to an embodiment compared to a Gore Preclude Membrane.
Figure 15B:
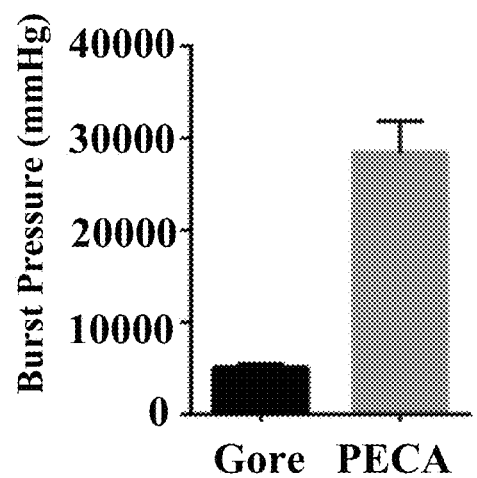
FIG. 15B illustrates a leaflet having a burst pressure according to an embodiment compared to a Gore Preclude Membrane.
Figure 15C:
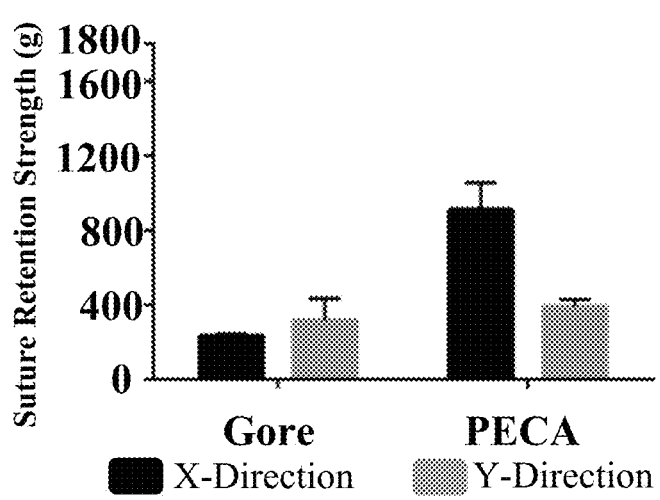
FIG. 15C illustrates a leaflet having a suture retention strength according to an embodiment compared to a Gore Preclude Membrane.
Figure 15D:
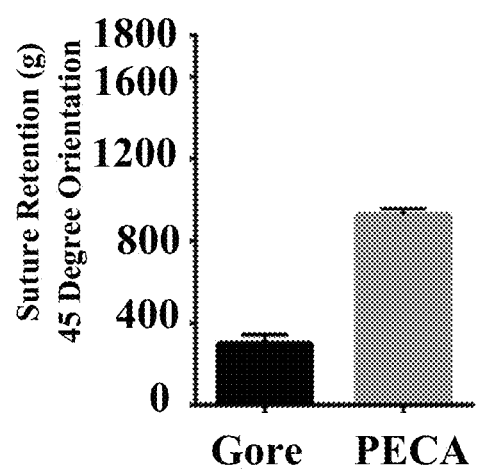
FIG. 15D illustrates a leaflet having a suture retention 45 degree orientation according to an embodiment compared to a Gore Preclude Membrane.
Figure 16A:
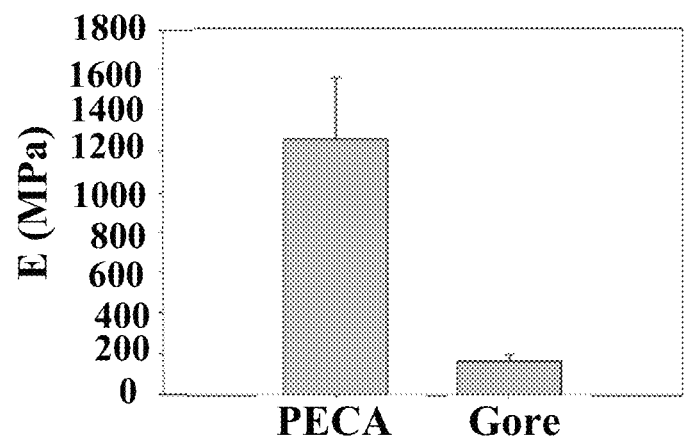
FIG. 16A illustrates a leaflet having a bending modulus in MPa according to an embodiment compared to a Gore Preclude.
Figure 16B:
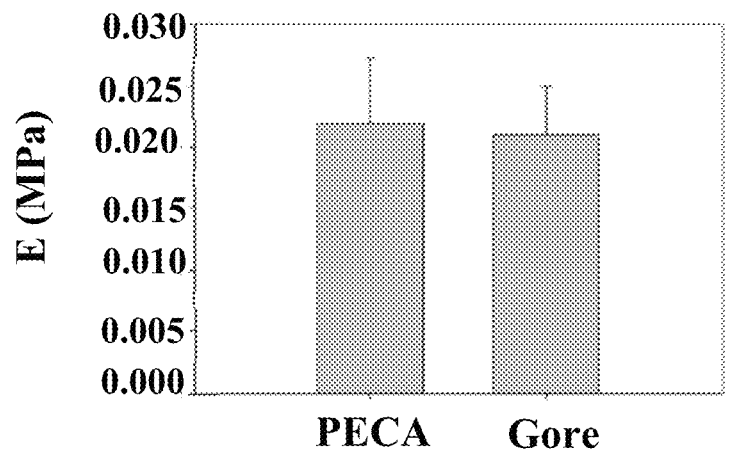
FIG. 16B illustrates a leaflet having a bending modulus in N mm$^2$ according to an embodiment compared to a Gore Preclude.
Figure 17A:
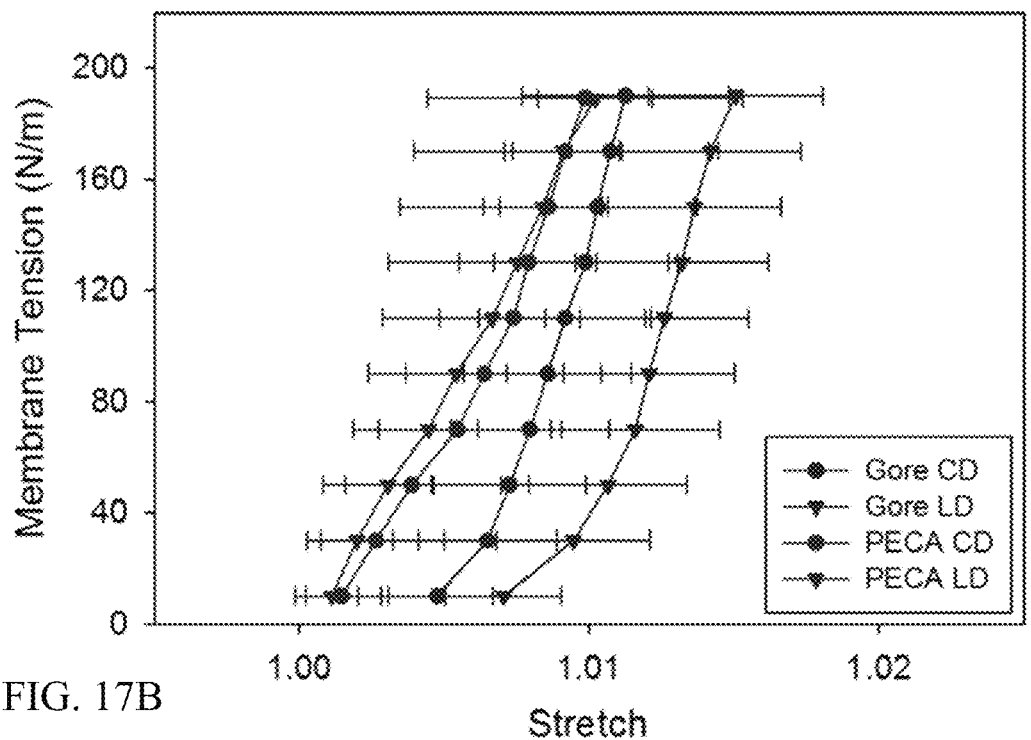
FIG. 17A depicts a leaflet having a membrane tension according to an embodiment compared to a Gore Preclude Membrane.
Figure 17B:
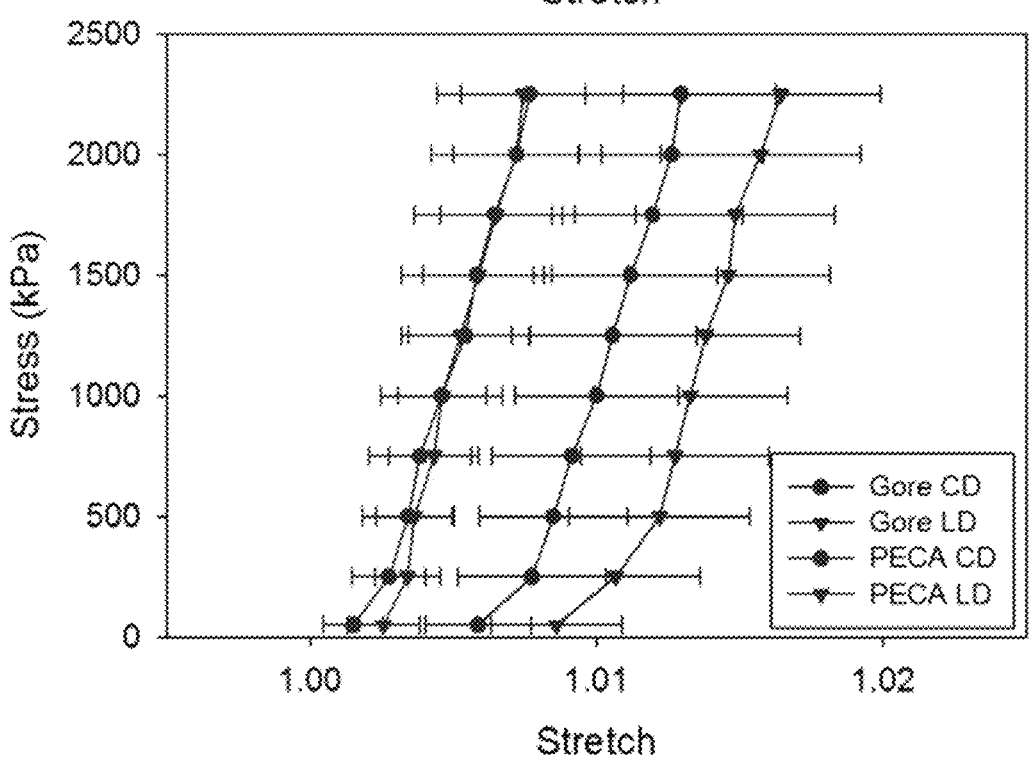
FIG. 17B depicts a leaflet having a stress according to an embodiment compared to a Gore Preclude Membrane.

Under similar conditions described above, and when compared to Gore, the PECA Leaflet Material has improved ultimate tensile stress in both the X-direction (dark bars) and Y-direction (gray bars) as illustrated in FIG. 15A, improved burst pressure as illustrated in FIG. 15B, improved suture retention strength in both the X-direction (dark bars) and Y-direction (gray bars) as illustrated in FIG. 15C, and improved suture retention in a 45 degree orientation as illustrated in FIG. 15D. Additionally, when compared to Gore, the PECA Leaflet Material displays augmented bending modulus measured in MPa as illustrated in FIG. 16A, and no change in bending modulus measured in N mm$^2$ (which accounts for the Moment of Inertia) as illustrated in FIG. 16B. The PECA Leaflet Material further displays reduced membrane tension compared to Gore as depicted in FIG. 17A, and reduced stress as depicted in FIG. 17B.

Example 2

The objective of the study was to assess the thrombogenic properties of the PECA Leaflet Material as described in Example 1 and compare it to the Gore commercially available membrane material that is intended to resist thrombosis.

The PECA Leaflet Material comprises a multi-layer leaflet made of ePTFE having a surface porosity of about 4% (about 2% of Side A and about 6% on side B), a total thickness of 0.045 mm, wherein the multi-layers of the leaflet are anisotropic with orientations that are rotated by less than 90 degrees, but greater than 10 degrees, relative to each other. The PECA Leaflet Material was compared to the Gore Preclude Membrane having a total thickness of 0.1 mm in a blood-contacting environment. In order to compare and assess the differential activated platelet and fibroblast growth on the material, multiple samples (n=3) of each material were cut into 1×1 cm pieces and prepared for blood exposure in 2 ml Centrifuge tubes and weighed. Sheep blood was then treated with 0.5 units of heparin per mL of blood. The blood was then re-calcified using Calcium Chloride and an arterial blood gas analyzer was used to read calcium levels until a reading of 1-1.5 mmol/L was attained. This blood was added to the 2 mL centrifuge tubes with the different materials to be tested & filled to top to avoid the presence of air. The tubes placed on a rocker at 37° C. All samples were removed after 15 mins of incubation and were rinsed for 5 minutes five times. The first rinse was with 100 units/mL heparin solution in saline, and the other four rinsing procedures were performed with saline. These samples were then collected and prepared appropriately for visualization under Scanning Electron Microscopy (SEM) and a qualitative analysis was performed.

A significantly lower amount of activated platelet adhesion and fibroblastic activity was observed in the PECA Leaflet Material (FIG. 18A depicts Side A, low magnification; FIG. 18C depicts Side A, high magnification; FIG. 18B depicts Side B, low magnification; FIG. 18D depicts Side B, high magnification) when compared to Gore (FIG. 18E depicts Side A, low magnification; FIG. 18G depicts Side A, high magnification; FIG. 18F depicts Side B, low magnification; FIG. 18H depicts Side B, high magnification).

The SEM images confirm the PECA Leaflet Material displays improved microstructure and material properties and is more resistant to thrombosis compared to the Gore Preclude Membrane. It was concluded qualitatively that the PECA Leaflet Material showed little or no signs of thrombosis or fibrotic growth as the material itself was visible throughout the image without signs of platelets, fibrin, or cells. The Gore materials showed significant amounts of activated platelet growth along with fibrous growth seen as a result of thrombosis of blood on the material.

Example 3

A method of making a conduit, valve, or leaflet having a multiple layers of material is exemplified below. The inner surface of a first layer of material is superposed to the outer surface of a second layer of material. The first layer and the second layer are attached by providing heat beyond the melting temperature of at least one of the first layer or the second layer. The melting temperature of at least one of the first layer or the second layer may be determined by routine experimentation of one skilled in the art.

Alternatively, a plate is provided to support the first layer of material when superposed to the second material. Heat is then provided, beyond the melting temperature of at least one of the first layer or the second layer, to attach the first layer and the second layer. Following removal of the plate and heat, the multiple layers of material may be formed into a conduit, a valve, or a leaflet by any cutting method known in the art. Non-limiting examples of cutting methods include the use of scissors, a blade, die cutting, laser cutting or combinations thereof.

For example, a valved conduit may be made by extruding two tubular layers, and then placed such that there is an outer and inner concentric layer. An inner and an outer concentric cylindrical fixture are placed and heated to beyond the melting temperature of at least one layer.

Leaflets may be made by cutting the tubular layers and placing them to form sheets, one lying on top of the other. Plates are placed sandwiching the two layers and heat is applied beyond the melting temperature of at least one layer. When the plates or heating cylinders are removed, the layers are sintered and may be formed into leaflets by hand (with scissors, blade, etc.), by die cut, by laser cut, or the like.

Example 4

The objective of the study was to assess the luminal and abluminal surface thrombogenic properties of a multi-layer conduit (termed PECA Conduit) as described above. The luminal surface of the multi-layer conduit has a surface porosity of less than 10%, and the abluminal surface of the multi-layer conduit has a surface porosity of greater than 20%. The multi-layer conduit is compared to the Gore commercially available membrane material that is intended to resist thrombosis, and a BARD Impra Conduit commercially available graft that is intended to allow some thrombosis.

The PECA Conduit comprises a multi-layer conduit made of ePTFE having a luminal surface porosity of about 4%, an abluminal surface porosity of greater than 20%, a total luminal-layer thickness of 0.045 mm, and a total abluminal layer thickness of about 1 mm. The PECA Conduit was compared to the Gore Preclude Membrane having a total thickness of 0.1 mm in a blood-contacting environment and the BARD Impra Conduit having a surface porosity of >20%. In order to compare and assess the differential activated platelet and fibroblast growth on the material, multiple samples (n=3) of each material were cut into 1×1 cm pieces and prepared for blood exposure in 2 ml Centrifuge tubes and weighed. Sheep blood was then treated with 0.5 units of heparin per mL of blood. The blood was then re-calcified using Calcium Chloride and an arterial blood gas analyzer was used to read calcium levels until a reading of 1-1.5 mmol/L was attained. This blood was added to the 2 mL centrifuge tubes with the different materials to be tested & filled to top to avoid the presence of air. The tubes placed on a rocker at 37° C. All samples were removed after 15 mins of incubation and were rinsed for 5 minutes five times. The first rinse was with 100 units/mL heparin solution in saline, and the other four rinsing procedures were performed with saline. These samples were then collected and prepared appropriately for visualization under Scanning Electron Microscopy (SEM) and a qualitative analysis was performed.

Figure 19A:
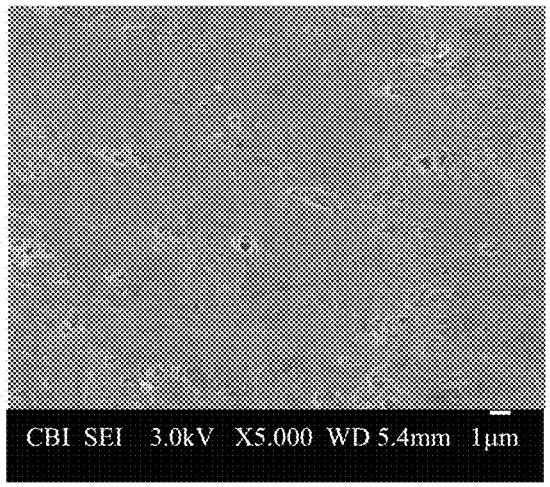
FIG. 19A illustrates a multi-layer conduit having a luminal surface with reduced thrombogenicity according to an embodiment.
Figure 19B:
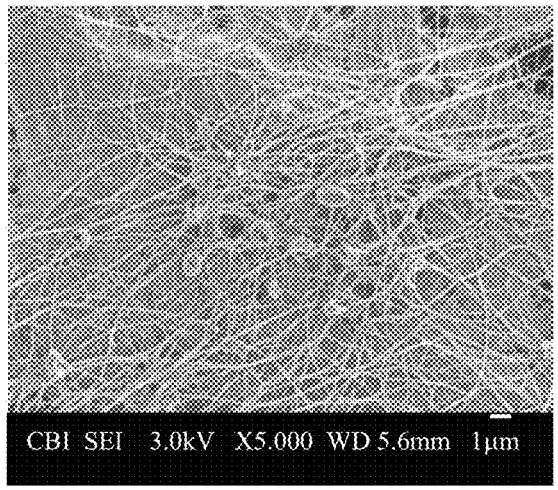
FIG. 19B illustrates a multi-layer conduit having an abluminal surface with reduced thrombogenicity according to an embodiment.
Figure 19C:
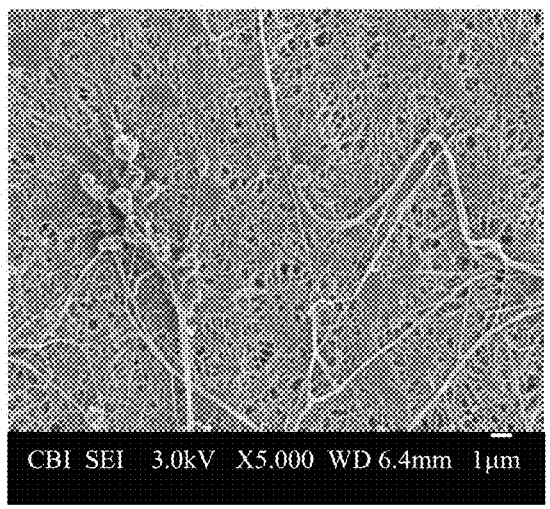
FIG. 19C illustrates a Gore Preclude Membrane having thrombogenicity.
Figure 19D:
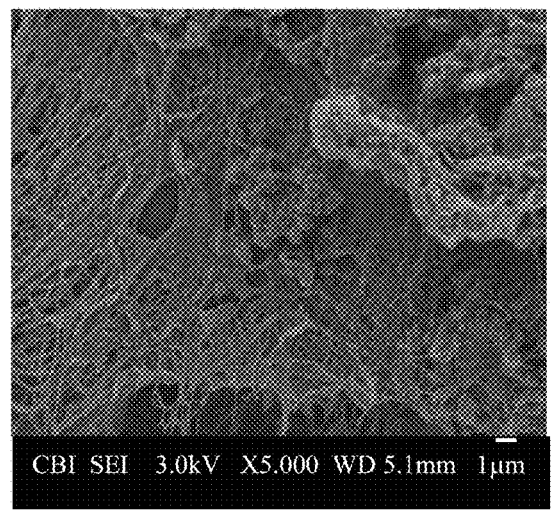
FIG. 19D illustrates a BARD Impra Conduit having thrombogenicity.

A significantly lower amount of activated platelet adhesion and fibroblastic activity was observed in the luminal surface of the PECA Conduit (FIG. 19A) when compared to the Gore Preclude Membrane (FIG. 19C). Higher amounts of growth were seen on both the abluminal surface of the PECA Conduit (FIG. 19B) and BARD Impra Conduit (FIG. 19D).

The SEM images confirm the PECA Conduit displays a luminal surface that features improved microstructure and material properties and is more resistant to thrombosis compared to the Gore Preclude Membrane, while maintaining an abluminal surface which is less resistant to thrombosis than Gore Preclude Membrane. It was concluded qualitatively that the PECA Conduit luminal surface showed little or no signs of thrombosis or fibrotic growth as the material itself was visible throughout the image without signs of platelets, fibrin, or cells, while the abluminal surface did allow for some thrombosis and/or fibrotic growth. The Gore Preclude Membrane materials showed a small amount of thrombosis, while the BARD Impra Conduit showed the most thrombosis.

What is claimed is:

1. A valve suitable for implantation into a human or animal comprising one or more leaflets, wherein the one or more leaflets are constructed from a layer of a material which has a surface porosity of 1.9% to less than 15%, wherein the one or more leaflets comprise more than one layer of the material, and wherein at least two layers of the more than one layer are anisotropic.

2. The valve of claim 1, wherein the material is a fluoropolymer.

3. The valve of claim 1, wherein the layer includes a surface coating.

4. The valve of claim 1, wherein the layer has an average pore area of less than or about 1 square micron.

5. The valve of claim 1, wherein the layer has an average pore diameter of less than or about 1 micron.

6. The valve of claim 1, wherein the layer has a thickness of less than or about 0.1 mm.

7. The valve of claim 1, wherein each layer is separably manufacturable, and wherein the at least two layers of the more than one layer have orientations that are offset by an angle of at least 10 degrees.

8. The valve of claim 7, wherein the orientations of the at least two layers are offset by about 10 degrees to about 90 degrees relative to each other.

9. The valve of claim 1, wherein the one or more leaflets have a total thickness of less than or about 0.1 mm.

10. The valve of claim 1, wherein the one or more leaflets have a suture retention strength from about 320 g to about 1,172 g.

11. A valved conduit suitable for implantation into a human or animal comprising:
a conduit having an inner surface and an outer surface;
a valve attached to the inner surface of the conduit at a plurality of attachment points, the valve further comprising one or more leaflets,
wherein the one or more leaflets are constructed from a layer of a material which has a surface porosity of 1.9% to less than 15%, wherein the one or more leaflets comprise more than one layer of the material, and wherein at least two layers of the more than one layer are anisotropic.

12. The valved conduit of claim 11, wherein the conduit is a stent.

13. The valved conduit of claim 11, wherein the material is a fluoropolymer.

14. The valved conduit of claim 11, wherein the layer includes a surface coating.

15. The valved conduit of claim 11, wherein the layer has an average pore area less than or about 1 square micron.

16. The valved conduit of claim 11, wherein the layer has an average pore diameter less than or about 1 micron.

17. The valved conduit of claim 11, wherein the layer has a thickness of less than or about 0.1 mm.

18. The valved conduit of claim 11, wherein each layer is separably manufacturable, and wherein the at least two layers of the more than one layer have orientations that are offset by an angle of at least 10 degrees.

19. The valved conduit of claim 18, wherein the orientations of the at least two layers are offset by about 10 degrees to about 90 degrees relative to each other.

20. The valved conduit of claim 11, wherein the one or more leaflets have a total thickness less than or about 0.1 mm.

21. The valve of claim 11, wherein the one or more leaflets have a suture retention strength from about 320 g to about 1,172 g.

22. A valved conduit suitable for implantation into a human or animal comprising:
a fluoropolymer conduit having an inner surface and an outer surface;
a valve attached to the inner surface of the conduit at a plurality of attachment points, wherein the valve includes one or more leaflets,
wherein the one or more leaflets are constructed from at least two layers of a fluoropolymer having a surface porosity of 1.9% to about 7% and a total thickness of about 0.045 mm, and
wherein the at least two layers are anisotropic with orientations that offset by an angle of at least 10 degrees.

* * * * *